(12) United States Patent
Connor et al.

(10) Patent No.: US 8,778,878 B2
(45) Date of Patent: *Jul. 15, 2014

(54) USE OF FERRITIN TO TREAT IRON DISORDERS

(75) Inventors: James R. Connor, Hershey, PA (US); Ralph Lauren Keil, Palmyra, PA (US)

(73) Assignee: Chyna, LLC, Hershey, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/114,429

(22) Filed: May 24, 2011

(65) Prior Publication Data

US 2011/0287033 A1 Nov. 24, 2011

Related U.S. Application Data

(63) Continuation-in-part of application No. 12/021,922, filed on Jan. 29, 2008, now Pat. No. 8,071,542.

(60) Provisional application No. 60/886,972, filed on Jan. 29, 2007, provisional application No. 60/984,007, filed on Oct. 31, 2007.

(51) Int. Cl.
*A61K 38/00* (2006.01)
*C12N 15/09* (2006.01)

(52) U.S. Cl.
USPC ......... 514/5.4; 514/1.2; 424/93.51; 424/93.2; 435/69.1; 435/69.6

(58) Field of Classification Search
CPC combination set(s) only.
See application file for complete search history.

(56) References Cited

PUBLICATIONS

Beard, John L., et al., "Purified Ferritin and Soybean Meal Can be Sources of Iron for Treating Iron Deficiency in Rats", The Journal of Nutrition, vol. 126, Oct. 1996, pp. 154-160.
Chakravarti, Sumone, et al., "Tim-2 Regulates T Helper Type 2 Responses and Autoimmunity", The Journal of Experimental Medicine, vol. 202, No. 3, Aug. 2005, pp. 437-444.
Chang, Yu-Jung, et al., "Recovery from Iron Deficiency in Rats by the Intake of Recombinant Yeast Producing Human H-ferritin", Nutrition, vol. 21, 2005, pp. 520-524.
Chen, Thomas T., et al., "Tim-2 is Expressed on B Cells and in Liver and Kidney and is a Receptor for H-ferritin Endocytosis", The Journal of Experimental Medicine, vol. 202, No. 7, Oct. 3, 2005, pp. 955-965.
Fisher, J., et al., "Ferritin: A Novel Mechanism for Delivery of Iron to the Brain and Other Organs", American Journal of Physiology—Cell Physiology, vol. 293, Aug. 2007, pp. C641-C649.
Hinnen, Albert, et al., "Transformation of Yeast", Proceedings of the National Academy of Sciences of the United States of America, vol. 75, No. 4, Apr. 1978, pp. 1929-1933.
Hulet, S.W., et al., "Characterization and Distribution of Ferritin Binding Sites in the Adult Mouse Brain", Journal of Neurochemistry, vol. 72, No. 2, 1999, pp. 868-874.
Hulet, S.W., et al., "Oligodendrocyte Progenitor Cells Internalize Ferritin Via Clathrin-Dependent Receptor Mediated Endocytosis", Journal of Neuroscience Research, vol. 61, 2000, pp. 52-60.
Hulet, S.W., et al., Distribution of Transferrin and Ferritin Binding in Normal and Multiple Sclerotic Human Brains, Journal of the Neurological Sciences, vol. 165, 1999, pp. 48-55.
Kim, Kyung-Suk, et al., "Enhanced Expression of High-affinity Iron Transporters via H-ferritin Production in Yeast", Journal of Biochemistry and Molecular Biology, vol. 40, No. 1, Jan. 2007, pp. 82-87.
Seo, H.Y., et al., "Enhanced Expression and Functional Characterization of the Human Ferritin H- and L-chain Genes in *Saccharomyces cerevisiae*", Applied Microbiology and Biotechnology, vol. 63, 2003, pp. 57-63.
Thompson, Khristy J., et al., "Regulation, Mechanisms and Proposed Function of Ferritin Translocation to Cell Nuclei", Journal of Cell Science, vol. 115, 2002, pp. 2165-2177.
Todorich, Bozho, et al., "Tim-2 is the Receptor for H-ferritin on Oligodendrocytes", Journal of Neurochemistry, vol. 107, 2008, pp. 1495-1505.
Iron Deficiency Anemia—University of Maryland Medical Center website—http://www.umm.edu/blood/aneiron.htm dated Oct. 26, 2010, 2 pages.

*Primary Examiner* — Daniel C Gamett
(74) *Attorney, Agent, or Firm* — McCarter & English

(57) ABSTRACT

Methods and compositions for treating an iron disorder in a patient are presented, including methods for delivering a therapeutically effective amount of iron to the brain. Iron disorders that may be treated by these methods include iron deficiency disorders and iron overload disorders. A recombinant yeast expressing human H-ferritin and a composition for treating an iron disorder comprising this recombinant yeast are also presented.

24 Claims, 20 Drawing Sheets
(5 of 20 Drawing Sheet(s) Filed in Color)

FIGURE 12
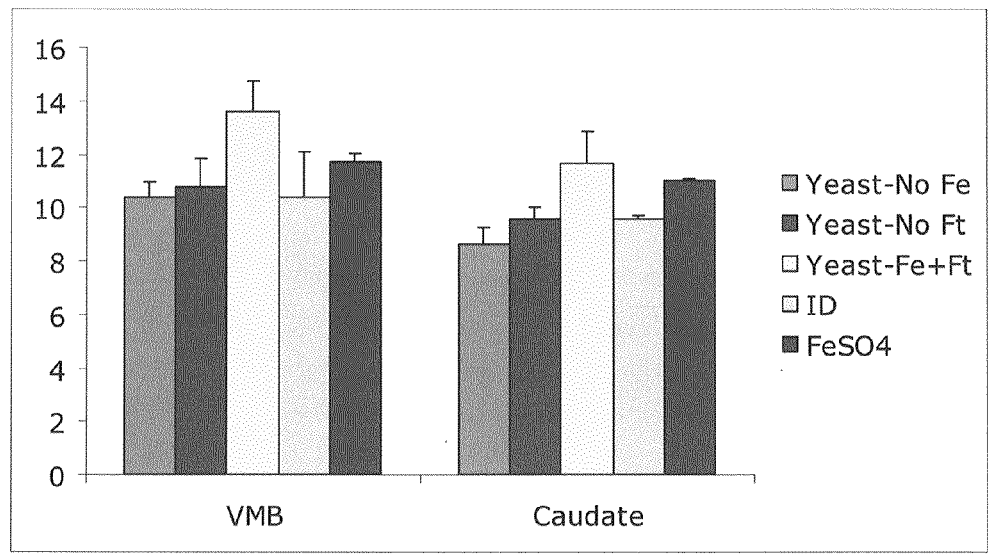
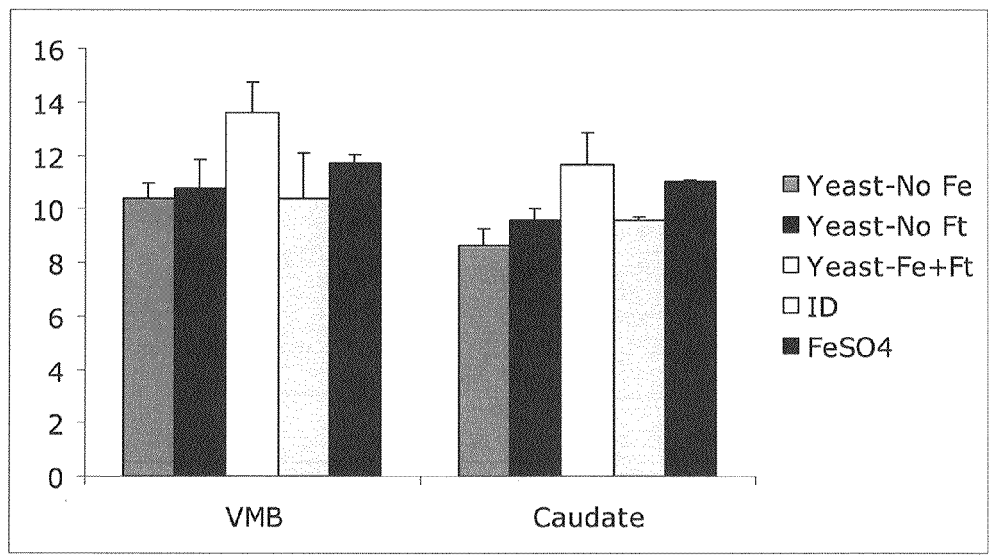

FIGURE 13
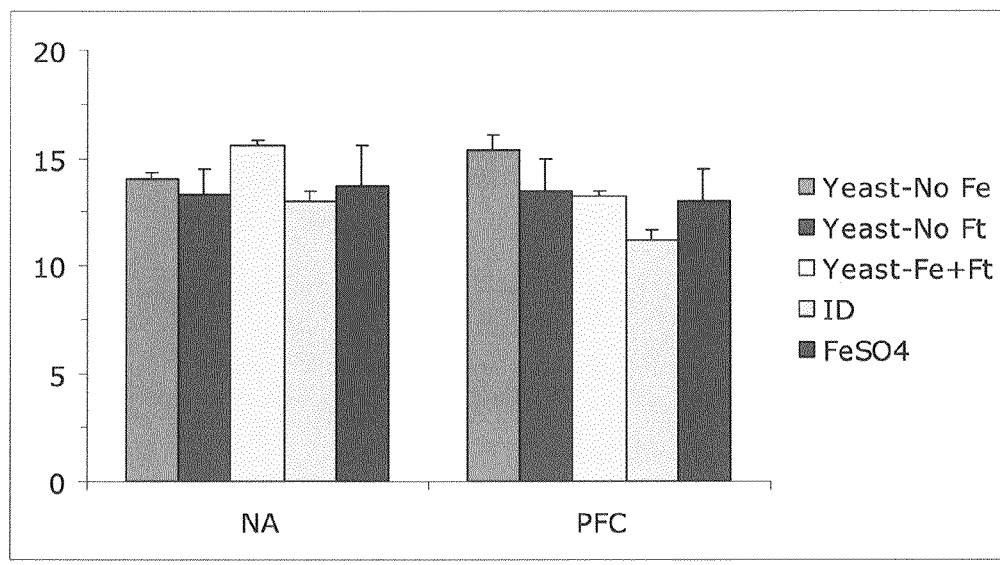
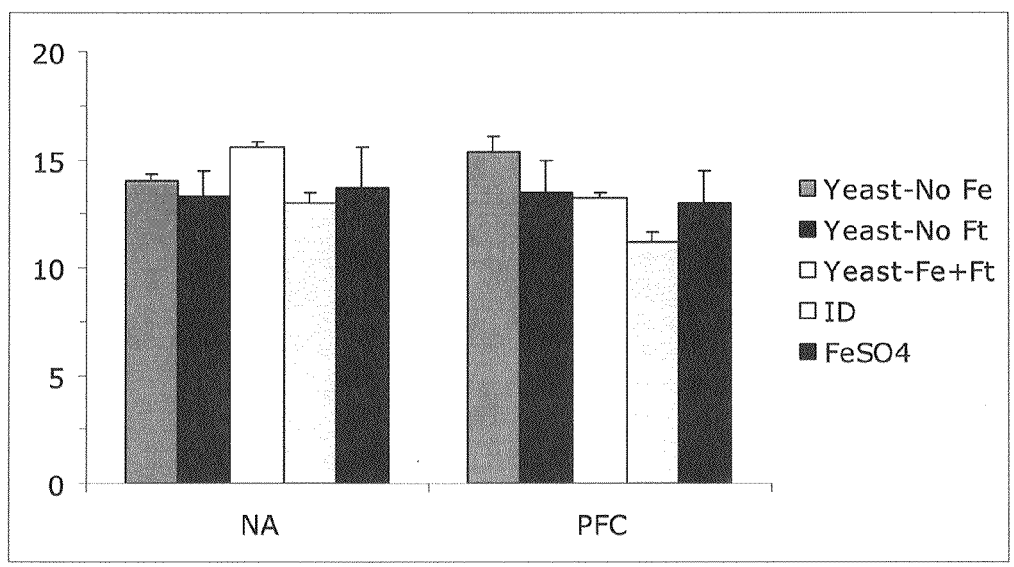

FIGURE 14A

MTTASTSQVRQNYHQDSEAAINRQINLELYASYVYLSMSYYFDRDDVALKNFAKYFLHQSHEER
EHAEKLMKLQNQRGGRIFLQDIKKPDCDDWESGLNAMECALHLEKNVNQSLLELHKLATDKNDP
HLCDFIETHYLNEQVKAIKELGDHVTNLRKMGAPESGLAEYLFDKHTLGDSDNES

FIGURE 14B

ATGGCTGATATC
GGATCCATACATATGACGACCGCGTCCACCTCGCAGGTGCGCCAGAACTACCACCAGGACTCAG
AGGCCGCCATCAACCGCCAGATCAACCTGGAGCTCTACGCCTCCTACGTTTACCTGTCCATGTC
TTACTACTTTGACCGCGATGATGTGGCTTTGAAGAACTTTGCCAAATACTTTCTTCACCAATCT
CATGAGGAGAGGGAACATGCTGAGAAACTGATGAAGCTGCAGAACCAACGAGGTGGCCGAATCT
TCCTTCAGGATATCAAGAAACCAGACTGTGATGACTGGGAGAGCGGGCTGAATGCAATGGAGTG
TGCATTACATTTGGAAAAAAATGTGAATCAGTCACTACTGGAACTGCACAAACTGGCCACTGAC
AAAAATGACCCCCATTTGTGTGACTTCATTGAGACACATTACCTGAATGAGCAGGTGAAAGCCA
TCAAAGAATTGGGTGACCACGTGACCAACTTGCGCAAGATGGGAGCGCCCGAATCTGGCTTGGC
GGAATATCTCTTTGACAAGCACACCCTGGGAGACAGTGATAATGAAAGCTAACCTAGGCACCTC
GAG

SEQUENCE LISTING

```
<160> NUMBER OF SEQ ID NOS: 2

<210> SEQ ID NO 1
<211> LENGTH: 591
<212> TYPE: DNA
<213> ORGANISM: Homo sapiens

<400> SEQUENCE: 1
atggctgata tcggatccat acatatgacg accgcgtcca cctcgcaggt gcgccagaac      60
taccaccagg actcagaggc cgccatcaac cgccagatca acctggagct ctacgcctcc     120
tacgtttacc tgtccatgtc ttactacttt gaccgcgatg atgtggcttt gaagaacttt    180
```

```
gccaaatact ttcttcacca atctcatgag gagagggaac atgctgagaa actgatgaag    240
ctgcagaacc aacgaggtgg ccgaatcttc cttcaggata tcaagaaacc agactgtgat    300
gactgggaga gcgggctgaa tgcaatggag tgtgcattac atttggaaaa aaatgtgaat    360
cagtcactac tggaactgca caaactggcc actgacaaaa atgaccccca tttgtgtgac    420
ttcattgaga cacattacct gaatgagcag gtgaaagcca tcaaagaatt gggtgaccac    480
gtgaccaact tgcgcaagat gggagcgccc gaatctggct tggcggaata tctctttgac    540
aagcacaccc tgggagacag tgataatgaa agctaaccta ggcacctcga g             591

<210> SEQ ID NO 2
<211> LENGTH: 183
<212> TYPE: PRT
<213> ORGANISM: Homo sapiens

<400> SEQUENCE: 2

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
        35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80

Ile Phe Leu Gln Asp Ile Lys Lys Pro Asp Cys Asp Asp Trp Glu Ser
            85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
            165                 170                 175

Gly Asp Ser Asp Asn Glu Ser
            180
```

USE OF FERRITIN TO TREAT IRON DISORDERS

CROSS-REFERENCE TO RELATED APPLICATIONS

This application is a continuation-in-part application of U.S. patent application Ser. No. 12/021,922, filed Jan. 29, 2008, now U.S. Pat. No. 8,071,542, which claims priority from U.S. Provisional Application Nos. 60/886,972 and 60/984,007, filed Jan. 29, 2007 and Oct. 31, 2007, respectively, each of which is incorporated herein, in entirety, by reference.

BACKGROUND OF THE INVENTION

Iron is an essential nutrient that is not only required for carrying oxygen to throughout the bloodstream but is also a vital component of enzymes necessary for oxidative respiration. Iron deficiency is the most common nutrient deficiency in the world, and it is present in 25% of children under the age of 2 (DeMaeyer, E. and Adiels-Tegman, M., *World Health Stat. Q.* 38: 302-316, 1985; Beard, J. and Stoltzfus, R., *J. Nutr.* 131: 563S-703S, 2000). The neurological sequelae of chronic, severe, childhood iron deficiency include poor school performance, decreased cognitive abilities, and behavior problems (Beard, J., and Connor, J., *Annu. Rev. Nutr.* 23: 41-58, 2003; Lozoff, B., et al., *Nutr. Rev.* 64: S34-S43, 2006), most of which persist following dietary iron supplementation (Felt, B., et al., *Behav. Brain Res.* 171: 261-270; Lozoff, B., et al., *Nutr. Rev.* 64: S34-S43, 2006). The brain has the highest rate of oxidative metabolism of any organ and requires relatively high quantities of iron. Dietary iron deficiencies during early postnatal development can result in both mental disorders and severe motor impairments that can persist into adulthood. The process of myelination seems to be particularly dependent on the availability of iron, especially during the critical growth period. (See, Hulet, S. W., et al., *J. Neurochem.* 72: 868-874, 1999 for citations).

A number of dietary iron supplements have been developed, but have limited efficacy because the iron is poorly absorbed or the supplement is dependent on environmental conditions to generate a consistent level of iron. The standard of care in developed countries is ingestion of 325 mg of ferrous sulfate three times a day. This very high dose of iron is necessary because of the poor absorption of iron in this form. However, because such a high dosing regimen results in gastrointestinal discomfort and a high rate of non-compliance, a need remains for a more efficient and cost-effective oral iron supplement for the treatment of iron-deficiency disorders.

Traditionally, transferrin has been considered the primary mechanism for cellular iron delivery, and a transferrin-mediated transport system has been identified in the blood-brain barrier (Jefferies W. A., et al. *Nature* 312: 162-163, 1984; Fishman J., et al., *J. Neurosci. Res.* 18: 299-304, 1987). However, transferrin-independent iron delivery to the brain has been suggested from experiments on hypotransferrinemic mice (Malecki E. A., et al., *J. Neurol. Sci.* 170: 112-118, 1999), and may involve ferritin.

Ferritin, the main intracellular iron storage protein in many prokaryotes and eukaryotes, is a large (nearly 480 kDa) multi-subunit complex comprising 24 polypeptide subunits. This iron storage complex, found in high concentrations in serum, is capable of containing as many as 4,500 atoms of iron ions ($Fe^{3+}$) within a hydrous ferric oxide core. In mammals, there are two distinct subunit classes, heavy (H) and light (L) type with a molecular weight of about 21 kDa and 19 kDa, respectively, which share about 54% sequence identity. The H and L subunits appear to have different functions: the L subunit enhances the stability of the iron core while the H subunit has a ferroxidase activity that appears to be necessary for the rapid uptake of ferrous iron. H-rich ferritins are localized in tissues undergoing rapid changes in local ion concentration. For example, expression of the H subunit is preferentially increased relative to the L subunit in cells undergoing differentiation, development, proliferation and metabolic stress.

The brain imposes heightened challenges to iron acquisition because of the highly developed tight junctions that bind neighboring endothelial cells that make up the brain microvasculature. These junctions prevent the paracellular flux of molecules into the brain. The resulting blood-brain barrier is a highly effective mechanism for protecting the brain from potentially harmful substances that circulate in the blood. A consequence of such a blockade, however, is that specific transport mechanisms must be designed for the many trophic substances, such as iron, that are required for normal brain function. In addition, traditional methods of measuring hemoglobin and hematocrit levels in blood samples do not address whether iron is crossing the blood-brain barrier or provide any indication of brain iron concentrations (Beard, et al., *J. Neurosci. Res.* 79: 254-261, 2005; Malecki, et al., *J. Neurosci. Res.* 56: 113-122, 1999).

Although H-ferritin has been shown to supply iron to iron-deficient rats, restoration of hemoglobin and hematocrit levels in animals fed H-ferritin in these studies was no better than in animals fed $FeSO_4$, the current standard of care. (Chang, Y-J., et al., *Nutrition* 21: 520-524, 2005). Therefore, a need remains for an improved method for treating iron-deficiency disorders.

SUMMARY OF THE INVENTION

Methods for treating an iron disorder in a patient, comprising administering to a patient in need thereof a therapeutically effective amount of a ferritin-iron complex are provided. A recombinant yeast comprising a nucleic acid sequence encoding human H-ferritin integrated into the yeast chromosome and a composition comprising the recombinant yeast are provided which may be used in these methods.

Methods for delivering a therapeutically effective amount of iron to the brain, comprising administering a ferritin-iron complex to a patient, whereby a therapeutically effective amount of iron is transported across the blood-brain barrier and delivered to the brain are provided.

Methods for using H-ferritin as a targeting moiety, comprising attaching H-ferritin to a liposome, whereby the liposome is targeted to the brain are further provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 12 shows the iron status of two developmentally important areas of the brain, the ventral midbrain and the caudate. The animals described in the Hb and Hct analyses (FIGS. 9 and 10) were sacrificed at 14 days of age and the iron concentration of the ventral midbrain (VMB) and the caudate was determined. The animals receiving the yeast that had been fortified with H-ferritin and supplemented with iron (Yeast-Fe+Ft) had more iron in both brain regions than any other group.

FIG. 13 represents iron levels in the nucleus accumbens (NA) and prefrontal cortex (PFC) regions of the brain. In this figure, the regional specificity of the iron delivered from the ferritin-fortified iron-supplemented yeast (Yeast-Fe+Ft) is apparent. In the NA (similar to the VMB and caudate shown in FIG. 12), the iron content is elevated compared to the other modes of iron delivery. In the PFC, however, the iron delivered from the ferritin-fortified iron-enriched yeast is similar to that found for the other groups.

FIG. 14A shows the amino acid sequence of human H-ferritin (SEQ ID NO: 1).

FIG. 14B shows the cDNA sequence of human H-ferritin (SEQ ID NO: 2). The start (ATG) and stop (TAA) codons are in bold, and the BamHI (at 5' end of sequence) and XhoI (at 3' end of sequence) restriction sites are underlined.

DETAILED DESCRIPTION OF THE INVENTION

Figure 1A:
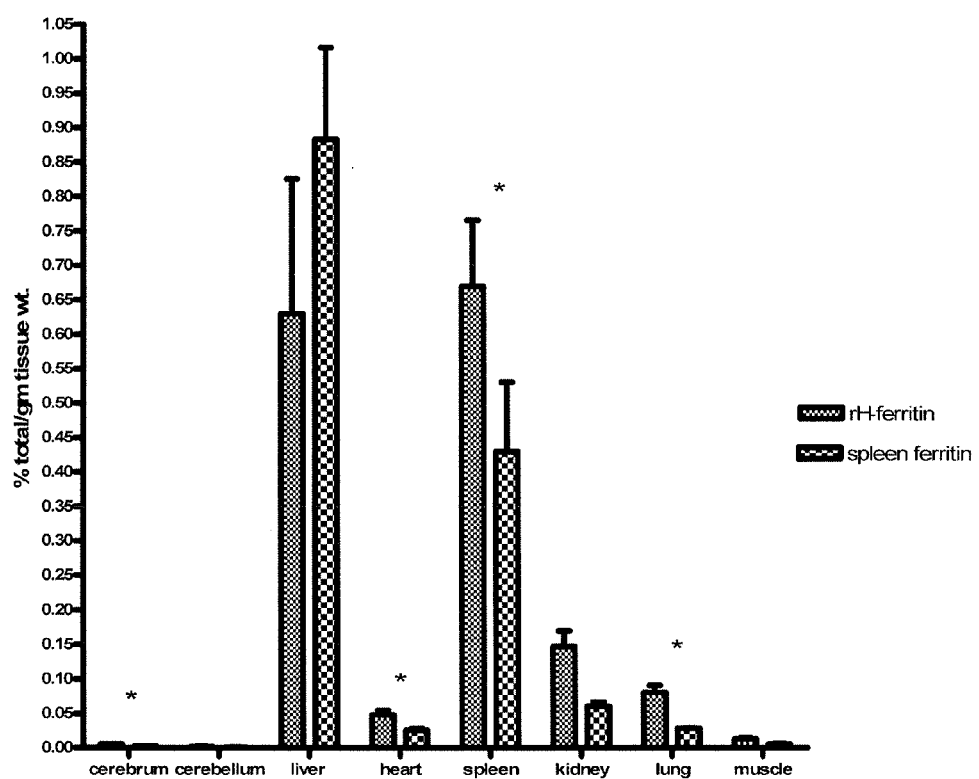
FIG. 1A shows the in vivo uptake of $^{59}Fe$ from recombinant human H-ferritin (rH-ferritin) as compared to horse spleen ferritin (spleen ferritin is enriched in L-ferritin) in organs after 48 hrs circulation. The $^{59}Fe$-labeled rH- or spleen ferritin was injected into adult rat tail veins and allowed to circulate for 48 hours. The amount of radioactivity was determined in 1.0 gram of each organ and the percent total/g tissue weight was determined by calculating the amount of μCi per gram of tissue compared to the total injected. The two brain structures are shown on this same scale to reveal the relative amounts. $p<0.05^*$. The mean value from 3 animals is presented ±S.E. (standard error).

A superior method for treating iron deficiency and other iron disorders that increases the bioavailability of iron and restores normal iron levels faster and more effectively than $FeSO_4$, the current standard of care, is described.

In one embodiment of the disclosure, a novel dietary approach to alleviating iron deficiency is presented. This approach stemmed from our discovery of receptors for H-ferritin in the gut and in the brain, and our demonstration that H-ferritin is the preferred manner of iron uptake, relative to L-rich ferritin. The gene sequence and protein structure of H-ferritin is highly conserved across the animal kingdom. Thus, the application of H-ferritin as an iron delivery protein is not limited to humans.

As used herein, an "iron disorder" includes a disorder or disease related to iron deficiency, iron uptake, and/or iron metabolism. Examples of iron-deficiency disorders include, but are not limited to, iron-deficiency anemia, such as iron-deficiency anemia caused by insufficient dietary intake or absorption of iron. Iron-deficiency anemia may be related to, for example, malnutrition, pregnancy (including the postpartum period), heavy uterine bleeding, chronic disease (including chronic kidney disease), cancer, renal dialysis, complications of gastric by-pass surgery, restless legs syndrome (RLS, Ekbom's Disease), multiple sclerosis, diabetes (e.g., Type I and Type II diabetes), insulin resistance, and attention deficit disorders. Iron to uptake and iron metabolism related disorders include, but are not limited to, iron overload, Huntington's disease, neurodegeneration with brain iron accumulation (NBIA), Alzheimer's disease, Parkinsons' disease, hypomyelination, and multiple sclerosis.

In one embodiment of the disclosure, the iron-deficiency disorder is related to is deficient iron levels in the brain, such as occurs in various neurological and neurodegenerative diseases including Parkinson's disease, Alzheimer's disease, RLS, suboptimal cognitive performance associated with anemia in women, depression and insomnia. In another embodiment, the iron-deficiency disorder comprises neurological deficit(s) associated with brain iron deficiency during postnatal development, including hypomyelination and slow brain development resulting from developmental iron deficiency leading to poor cognitive performance and motor impairments, and attention deficit hyperactivity disorder (ADHD).

Lack of iron and reduced dopamine synthesis in the brain are important factors in iron-deficiency disorders such as, for example, RLS and developmental iron deficiency in children. Dopamine is a neural transmitter synthesized in the brain that is essential for proper central nervous system (CNS) function. In the synthesis of dopamine, iron is a cofactor for the enzyme tyrosine hydroxylase, which is the rate-limiting step in dopamine metabolism (Cooper et al. (1991) *The Biochemical Basis of Neuropharmacology*, Oxford University Press, New York, N.Y.). Iron in the dopaminergic system appears to be an important component in RLS pathophysiology and in behavioral deficits in children, including ADHD. RLS patients have 65% less cerebral spinal fluid (CSF) ferritin and three-fold more CSF transferrin (iron transport blood protein), despite normal serum levels of ferritin and transferrin in serum of both RLS patients and controls. Iron concentrations vary throughout the brain, the site of dopamine synthesis; RLS patients have less iron in the substantia nigra and in the putamen regions of the brain. In general, the degree of decrease in serum ferritin levels is indicative of the severity of RLS symptoms. Reports also exist of decreased serum ferritin levels in children with ADHD.

The term "ferritin-iron complex" refers to a protein complex comprising multiple ferritin subunits and iron atoms. Suitable ferritin-iron complexes comprise mammalian H-ferritin and L-ferritin subunits. The amino acid sequences of H-ferritin subunits from various mammalian species have been identified (see, e.g., Orino Koichi et al., *Veterinary Biochem.* 42:7-11 (2005); Accession number: 06A006486). In one embodiment, the H-ferritin is human H-ferritin (SEQ ID NO: 1; see FIG. 14A). The H-ferritin can also be a naturally occurring or synthetic homologue or variant of human H-ferritin. In certain embodiments, the H-ferritin homologue has about 80% to about 100% sequence identity to human H-ferritin, such as at least 80%, 81%, 82%, 83%, 84%, 85%, 86%, 87%, 88%, 89%, 90%, 91%, 92%, 93%, 94%, 95%, 96%, 97%, 98%, or 99% sequence identity with human H-ferritin.

The H-ferritin homologue retains the ability to bind iron and form a multi-subunit ferritin-iron complex, but can be mutated to provide varying binding and disassociation strengths between the iron and the ferritin. The ferritin-iron complex comprises H-ferritin subunits, but can also comprise some L-ferritin subunits. In certain embodiments, the ferritin subunit component of the complex comprises at least 20% H-ferritin as compared to L-ferritin, such as about 20%, 30%, 40%, 50%, 60%, 70%, 80%, 90%, or 100% H-ferritin as compared to L-ferritin. In one embodiment, all of the ferritin subunits in the ferritin-iron complex (i.e. 100% of the ferritin subunits) are H-ferritin. The H-ferritin can be recombinant H-ferritin. For example, in one embodiment the H-ferritin can be human H-ferritin, or a homologue thereof, produced in a yeast strain comprising a polynucleotide sequence encoding the H-ferritin under the control of an appropriate yeast promoter. The H-ferritin produced in yeast can be purified for therapeutic use using standard methods of protein purification.

The iron in the ferritin-iron complex can be an iron molecule, or can be in the form of an iron-containing complex. "Iron-containing complexes" or "iron complexes" are compounds that contain iron in the (II) or (III) oxidation state, complexed with an organic compound. Iron complexes include iron polymer complexes, iron carbohydrate complexes, and iron aminoglycosan complexes. These complexes are commercially available and/or can be synthesized by methods known in the art.

Examples of iron carbohydrate complexes include iron saccharide complexes, iron oligosaccharide complexes, and iron polysaccharide complexes, such as iron carboxymaltose, iron sucrose, iron polyisomaltose (iron dextran), iron polymaltose (iron dextrin), iron gluconate, iron sorbital, and iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

Examples of iron aminoglycosan complexes include iron chondroitin sulfate, iron dermatin sulfate, iron keratan sulfate, which may be further complexed with other compounds and mixtures thereof. Examples of iron polymer complexes include iron hyaluronic acid, iron protein complexes, and mixtures thereof.

"Treatment" or "treating," as used herein, refers to complete elimination as well as to any clinically or quantitatively measurable reduction in the condition for which the patient or subject is being treated. "Treatment" is an intervention performed with the intention of preventing the development or altering the pathology or symptoms of a disorder. Accordingly, "treatment" refers to both therapeutic treatment and prophylactic or preventive measures. "Treatment" may also be specified as palliative care. Those in need of treatment include those already with one or more iron-deficiency disorder as well as those in which the disorder is to be prevented.

In treating a patient in need thereof, a therapeutically effective amount of the present ferritin-iron composition is administered thereto in accordance with the present invention. As used herein, the term "therapeutically effective amount" is an amount of the composition indicated for treatment while not exceeding an amount that may cause significant adverse effects. Methods for evaluating the effectiveness of therapeutic treatments are known to those of skill in the art.

A "patient in need thereof" refers to any patient or subject who could benefit from the inventive method of treatment. In certain embodiments, a patient in need thereof is a patient predisposed for the development of one or more iron-deficiency disorders, a subject having one or more iron-deficiency disorders but not exhibiting any clinical symptoms, or a subject having one or more iron-deficiency disorders and suffering from the symptoms of the one or more iron-deficiency disorders. The patient in need thereof may be a mammal, such as a human, a dog, a cat, a cow, a horse, a pig, a rodent, or a primate. In one embodiment, the patient is a human. In certain embodiments, the inventive methods find use in experimental animals, in veterinary and animal husbandry applications, and/or in the development of animal models for disease.

Doses to be administered are variable according to the treatment period, frequency of administration, the host, and the nature and severity of the disorder. The dose can be determined by one of skill in the art without an undue amount of experimentation. The compositions of the invention are administered in dosage concentrations sufficient to ensure the release of a sufficient dosage unit of the ferritin-iron complex into the patient to provide the desired treatment of the iron-deficiency disorder. The actual dosage administered will be determined by physical and physiological factors such as age, body weight, severity of condition, and/or clinical history of the patient. The active ingredients may be administered to achieve in vivo plasma concentrations of the ferritin-iron complex from about 50 µM to about 1000 µM. For example, the methods of the present invention may use compositions to provide from about 0.1 to about 1,000 or from about 1 to about 100 mg/kg body weight/day of the ferritin-iron complex, such as about 30 mg/kg body weight/day of the ferritin-iron complex. It will be understood, however, that dosage levels that deviate from the ranges provided may also be suitable in the treatment of a given disorder.

The ferritin-iron complexes of the present invention may be in any form suitable for administration. Such administrable forms include tablets, buffered tablets, pills, capsules, enteric-coated capsules, dragees, cachets, powders, granules, aerosols, liposomes, suppositories, creams, lotions, ointments, skin patches, parenterals, lozenges, oral liquids such as suspensions, solutions and emulsions (oil-in-water or water-in-oil), ophthalmic liquids and injectable liquids, or sustained-release forms thereof, and aerosols. The desired dose may be provided in several increments at regular intervals throughout the day, by continuous infusion, or by sustained release formulations, or may be presented as a bolus, electuary or paste.

In one embodiment, a pharmaceutical or nutraceutical composition or formulation comprising the ferritin-iron complexes is prepared by admixture with one or more pharmaceutically acceptable carriers. In some cases, the ferritin-iron complex may be delivered as a composition comprising ferritin-iron complexes and the buffer in which the iron molecules and the ferritin molecules were dissolved in to order to allow for iron-ferritin binding (i.e. formation of the ferritin-iron complexes). However, other products may be added, if desired, to maximize iron delivery, preservation, or to optimize a particular method of delivery. In addition, the present invention includes use of combination compositions comprising the ferritin-iron complexes as described herein in combination with other agents suitable for the treatment of iron-deficiency disorders.

As used herein, "pharmaceutically acceptable" means acceptable for use in the pharmaceutical and veterinary arts, compatible with other ingredients of the formulation, and not toxic or otherwise unacceptable commensurate with a reasonable benefit/risk ratio. A "pharmaceutically acceptable carrier" or "diluent" includes any and all solvents, dispersion media, coatings, antibacterial and anti-fungal agents, isotonic and absorption delaying agents, and the like, compatible with pharmaceutical administration of a composition comprising ferritin-iron complexes. Examples of such carriers or diluents include, but are not limited to, water, saline, Finger's solutions and dextrose solution. The volume of the pharmaceutical composition is based on the intended mode of administration and the safe volume for the individual patient, as determined by a medical professional.

The selection of carrier also depends on the intended mode of administration. Compositions of the present invention may be administered by any of a number of convenient means including, but not limited to, systemic administration (e.g., intravenous injection, intraparenteral injection, inhalation, transdermal delivery, oral delivery, nasal delivery, rectal delivery) and/or local administration (e.g., direct injection into a target tissue, delivery into a tissue via cannula, delivery into a target tissue by implantation of a time-release material), delivery into a tissue by a pump, etc., orally, parenterally, intraosseously, into the cerebrospinal fluid, or the like. Further modes of administration include buccal, sublingual, vaginal, subcutaneous, intramuscular, or intradermal administration.

In one embodiment, compositions to be administered orally are prepared using substances that are suitably combined with ferritin-iron complexes for oral ingestion. Such substances include, without limitation, sugars, such as lactose (hydrous, fast flow), glucose and sucrose; starches such as corn starch and potato starch; cellulose and derivatives thereof, including microcrystalline cellulose, sodium carboxymethylcellulose, ethylcellulose and cellulose acetates; powdered tragacanth; colloidal silicon dioxide; croscarmellose sodium; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbitol, mannitol and polyethylene glycol; agar; alginic acids; antacids such as aluminum hydroxide or magnesium hydroxide; buffers such as sodium citrate, acetate, or bicarbonate; water; isotonic saline and phosphate buffer solutions. Wetting agents, lubricants such as sodium lauryl sulfate, stabilizers, tableting agents, anti-oxidants, preservatives, coloring agents and flavoring agents may also be present.

Compositions or formulations suitable for parenteral administration include, but are not limited to, aqueous and non-aqueous, isotonic sterile injection solutions that may contain antioxidants, buffers, bacteriostats or solutes that render the formulation isotonic with blood; and aqueous and non-aqueous sterile suspensions that may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules or tablets, or the like.

Compositions or formulations suitable for intravenous administration comprise carriers such as physiological saline, bacteriostatic water, CREMOPHOR EL™ (BASF; Parsippany, N.J.) or phosphate buffered saline (PBS). The composition must be sterile and should be fluid so as to be administered using a syringe. Such compositions should be stable during manufacture and storage and must be preserved against contamination from microorganisms, such as bacteria and fungi. The carrier can be a dispersion medium containing, for example, water, polyol (such as glycerol, propylene glycol, and liquid polyethylene glycol), and other compatible, suitable mixtures. Various antibacterial and anti-fungal agents, for example, parabens, chlorobutanol, phenol, ascorbic acid, and thimerosal, can inhibit microorganism contamination. Isotonic agents such as sugars, polyalcohols, such as mannitol, sorbitol, and sodium chloride can be included in the composition. Compositions that can delay absorption include agents such as aluminum monostearate and gelatin. Methods of preparation of sterile solids for the preparation of sterile injectable solutions include vacuum drying and freeze-drying to yield a solid containing the ferritin-iron complex and any other desired ingredient.

Systemic administration can be, for example, transmucosal or transdermal. For transmucosal or transdermal administration, penetrants that can permeate the target barrier(s) are selected. Transmucosal penetrants include, detergents, bile salts, and fusidic acid derivatives. Nasal sprays or suppositories can be used for transmucosal administration. For transdermal administration, the active compounds are formulated into ointments, salves, gels, or creams.

Compositions comprising ferritin-iron complexes may be prepared with carriers that protect the complexes against rapid elimination from the body, such as a controlled release formulation, including implants and microencapsulated delivery systems. Biodegradable or biocompatible polymers can be used, such as ethylene vinyl acetate, polyanhydrides, polyglycolic acid, collagen, polyorthoesters, and polylactic acid. Such materials can be obtained commercially from sources including, but not limited to, ALZA Corporation (Mountain View, Calif.) and NOVA Pharmaceuticals, Inc. (Lake Elsinore, Calif.), or prepared by one of skill in the art.

Compositions for ophthalmic administration are prepared in suitable liquid carriers such as buffered or physiological saline, liposomes or basic amino acids. Creams, lotions and ointments may be prepared for topical application using an appropriate base such as triglyceride base, liposomes, or basic amino acids. Such creams, lotions and ointments may also contain a surface-active agent.

In an embodiment of the present invention, the ferritin-iron complexes are administered in the form of a strain of recombinant yeast expressing H-ferritin from a chromosomally integrated H-ferritin expression cassette. Recombinant yeast strains suitable for nutritional supplementation of iron can store iron in a form having high bioavailability for mammals, including humans. The strain of yeast includes those that meet the Generally Regarded As Safe (GRAS) requirements for human consumption. These may include, for example, yeast of the genera *Saccharomyces* and *Pichia*, as well as others that can be used in processes to produce therapeutic compounds. In this embodiment, the iron-storage gene (e.g., the H-ferritin coding to sequence) is placed under the control of an appropriate yeast promoter in an iron-storage expression cassette to produce high enough levels of the iron-storage protein for the yeast to serve as a suitable vehicle for iron supplementation. Construction of a specific recombinant yeast strain, which constitutively expresses rH-ferritin and provides significantly higher levels of bioavailable iron than standard dietary supplementation with $FeSO_4$ or spleen ferritin, is described in Example 2.

Suitable yeast promoters are known in the art, and include promoters that induce a high level of constitutive expression and promoters whose expression can be regulated by environmental conditions. In addition, the genetic constitution of the yeast can be further manipulated to achieve a variety of potentially advantageous outcomes. For example, proteolysis may be manipulated to enhance the stability of the iron-storage protein or iron transport mechanisms, including but not limited to those of the cell surface, the vacuole, or the mitochondria, can be manipulated to achieve desirable outcomes such as altering the iron concentration in specific cellular compartments. In addition, the yeast may be altered in other manners to manipulate the level of iron in the iron-storage protein or cellular compartments. The iron content of the yeast may be regulated by adding known amounts of an iron compound to the medium in which the yeast are grown. Using the recombinant yeast, iron supplementation for humans or other animals can be accomplished by any of a number of means including, but not limited to, consumption of the recombinant yeast as a nutritional supplement or consumption of ferritin-iron complexes purified or isolated from the recombinant yeast. The yeast may be grown specifically for the purpose of iron supplementation or they may be the by-product of another process (e.g., fermentation).

Alternatively, or in addition, ferritin-iron complexes can comprise rH-ferritin produced in other expression systems known in the art, including *E. coli*, baculovirus and transgenic plants and animals. In one embodiment, the ferritin-iron complexes can be formed by incubating ferritin subunits and iron molecules in a suitable buffer, followed by separating any unbound iron molecules from the resulting ferritin-iron complexes.

In certain embodiments, the ferritin-iron complex further comprises a targeting moiety, such as an antibody, aptamer, receptor, ligand, or binding fragment thereof. The targeting moiety can recognize one or more cell, tissue to and/or organ specific marker, thus mediating or improving delivery to a desired target or location in the body. In one embodiment, the ferritin-iron complex can comprise a fusion protein comprising a ferritin subunit, such as H-ferritin, fused with a targeting peptide. In another embodiment, the ferritin-iron complex may be delivered or administered encapsulated into a liposome, a liposomal construct, or other membrane-bound vesicle such as a red cell ghost. The liposome, liposomal construct or other vesicle can comprise a targeting moiety, such as an antibody or ligand specific for a particular cell surface protein or receptor (see above), incorporated into the liposome or vesicle. The targeting moiety can target the ferritin-iron complex, or the vesicle comprising the ferritin-iron complex, to the brain and/or to the blood-brain barrier. Examples of suitable targeting moieties include transferrin, interleukin-13 (for delivery to astrocytomas), and lipopolysaccharide (LPS).

In another embodiment of the invention, H-ferritin itself can be used to target other moieties. For example, H-ferritin can be attached to a biologically active agent in order to deliver that agent to the brain. In one embodiment, the H-ferritin peptide is fused to another biologically active peptide. Alternatively, or in addition, H-ferritin can be conjugated to liposomes or other vesicles to deliver the vesicles and the vesicle contents to the brain. In yet another embodiment, H-ferritin can be bound to agents such as contrast enhancing compounds to enhance visualization of the brain (e.g., white matter tracts and defects therein). Similar to the biologically active agents, the contrast enhancing compounds can be bound to or within the H-ferritin protein or encapsulated within liposomes or other vesicles that are targeted to H-ferritin receptors in the brain via liposome-conjugated H-ferritin acting as the receptor ligand.

In another embodiment of the invention, H-ferritin can be used to treat disorders related to excess iron or iron overload. Iron overload, clinically known as hemochromatosis, is associated with, for example, increased risk of cancer, heart failure, liver dysfunction, and diabetes. Iron overload in the brain can occur in a wide range of neurodegenerative diseases, such as Parkinson's disease, Alzheimer's disease, amyotrophic lateral sclerosis, Hallovordeen-Spatz, and Huntington's disease, as well as macular degeneration. Because of the significant iron binding capacity of H-ferritin, H-ferritin and/or multi-subunit complexes comprising H-ferritin can be used as an iron chelator. By "multi-subunit ferritin complex" is meant a protein complex comprising multiple ferritin subunits and optionally iron. The H-ferritin is mammalian ferritin or a homologue or variant thereof as defined above. The multi-subunit ferritin complexes can be prepared in a relatively iron-free environment so is that the resulting complex is at less than 100% of its total iron binding capacity. In certain embodiments, the complex is at 50% iron binding capacity or less, such as at about 50%, 40%, 30%, 20%, 10%, 5%, or 1% iron binding capacity. In one embodiment, the complex can be at about 0% iron binding capacity (i.e., apoferritin (iron-free ferritin) having 100% or close to 100% iron binding capacity remaining). The H-ferritin can be modified to decrease the likelihood that it will be recognized by any endogenous receptors or to increase excretion by the body. Such modifications are well within the expertise of someone practiced in the art and these modifications need not impact the ability of the protein to bind iron. The multi-subunit ferritin complexes suitable for use as iron chelators comprise H-ferritin subunits, but can also comprise some L-ferritin subunits. In certain embodiments, the multi-subunit ferritin complex comprises at least 20% H-ferritin as compared to L-ferritin, such as about 20%, 30%, 40%, 50%, 60%, 70%, 80%, 90%, or 100% H-ferritin as compared to L-ferritin.

The delivery of the multi-subunit ferritin complex for use as an iron chelator can include the same range of delivery mechanisms (e.g., consumption of yeast producing ferritin, administration of purified ferritin protein, targeting moieties and/or liposomes or other vesicles) as described above for delivery of ferritin-iron complexes to treat iron-deficiency disorders. The multi-subunit ferritin complex can be delivered to the gastrointestinal tract, within the cells lining the gastrointestinal tract, or within the bloodstream. Utilizing this approach, iron that would otherwise inappropriately gain access to the brain or other organs in an unregulated manner would be eliminated. Furthermore, chelating iron from the blood and systemic organs would promote a redistribution of iron within the body including release of iron from the brain. In some cases, apoferritin or ferritin complexes at less than 100% of total iron binding capacity can be delivered directly into the cerebrospinal fluid, the brain, or the bloodstream.

Ferritin has the capacity to bind not only iron but also a range of metals many to of which are toxic to the body. Thus another embodiment of this invention relates to use of apoferritin (or other multi-subunit ferritin complexes at less than 100% of total iron binding capacity) to reduce and eliminate potentially toxic metals from the gastrointestinal system, the blood, the brain and the body in general.

In blood transfusions, at least 15% of cells will lyse during the infusion process, releasing potentially damaging free iron. The transfusions are performed on patients who need red blood cells (RBCs) and thus are anemic. The present invention relates to a method for mixing apoferritin (or other multi-subunit ferritin complexes at less than 100% of total iron binding capacity) with the transfusate. This not only provides a chelator for the iron released due to cell lysis but also serves to make that iron available to the body in a more physiological or bioavailable form for treatment of anemia.

One patient population that requires frequent transfusions is patients with thalassemia. This population eventually suffers from liver damage due to excessive iron accumulation. H-ferritin and/or multi-subunit ferritin complexes comprising H-ferritin can help distribute the iron more effectively in the body thus limiting excessive accumulation in the liver. Another population receiving frequent blood transfusions is neonates, particularly premature neonates. Providing H-ferritin, multi-subunit ferritin complexes comprising H-ferritin, and/or ferritin-iron complexes with the transfusate would improve iron distribution generally as well as iron distribution to the brain.

The ferritin subunits, including H-ferritin subunits, can be expressed in the body of the patient. In this embodiment, the ferritin-iron complex would form in vivo. A number of plasmid carriers and transfection reagent systems are available to transfect cells ex vivo to generate either stable transformants or transiently transfected cells for reinfusion into the host animal or patient. Suitable expression plasmids are commercially available as are transfection reagents, many of the latter being cationic liposomes of one type or another. For in vivo as well as ex vivo gene transfer, such as gene therapy, suitable vectors are known in the art and include retroviral vectors, adenoviral vectors, adeno-associated viral vectors, lentiviral vectors, and electroporation systems.

Other aspects and advantages of the present invention will be understood upon consideration of the following illustrative examples. The examples are not to be construed in any way as limiting the scope of this invention. Those of skill in the art should, in light of the present disclosure, appreciate that changes can be made in the specific embodiments that are disclosed and still obtain a like or similar result without departing from the spirit and scope of the invention.

All references, publications and patent documents cited in this application are incorporated herein by reference.

EXAMPLES

Example 1

Ferritin Uptake and Transport

Methods
Ferritin Preparation

All the experiments in this example used recombinant human H-ferritin or horse spleen ferritin. The recombinant human H-ferritin was prepared by transforming chemically competent *E. coli* BL21(DE3) cells with a recombinant human H-ferritin plasmid. After the cells were grown, the protein was purified with a nickel protein filter column to a final concentration of 2.8 mg/ml. The horse spleen ferritin was obtained commercially (Sigma), and was chosen because it contains about 90:10 L- to H-ferritin subunits.

Cell Culture and Preparation of Endothelial Cell Monolayer

We used bovine retinal endothelial cells (BRECs) as an in vitro model of the blood-brain barrier (BBB) to test the hypothesis that ferritin can be transported across a layer of endothelial cells and to begin to address the mechanism of ferritin transport across the BBB. This well studied model has been shown to posses all of the necessary characteristics and attributes of a blood-neural barrier (Antonetti D. A., et al. *J. Neurochem.* 80: 667-677, 2002). Cow eyes were obtained from a local abattoir and the bovine retinal endothelial cells (BRECs) were isolated and processed according to a previously published procedure (Gardiner T. A., et al. *Lab Invest.* 72: 439-444, 1995). BRECs were grown in MCDB-131 media (Sigma, St. Louis, Mo., USA) supplemented with 10% FBS, 10 ng/ml EGF, 0.2 mg/ml IENDO GRO™ (VEC Technologies, Inc., Rensselaer, N.Y., USA), 0.09 mg/ml Heparin, antibiotic/antimycotic solution (Gibco, Rockville, Md., USA), and Tylosin antibiotic (Sigma). The cells are initially cultured in flasks until they reached at least 80% confluence. Subsequently, the BRECSs were gently trypsinized and grown to confluence on COSTAR® TRANSWELL™ 0.4 µm porous filters (Corning, Acton Mass.). Fibronectin was added at a concentration of 1 µg/cm$^2$ to promote adherence to the filter. The cells were then washed and stepped to serum-free EGF-free MCDB-131 media supplemented with 100 nm hydrocortisone for 72 hours. The addition of hydrocortisone to these cell cultures promoted the formation of tight junctions.

Ferritin Transport in the BBB Model

Pre-purified transferrin was purchased and resuspended to a final concentration of 2.5 mg/ml. About 250 µg of recombinant human H-ferritin, horse spleen ferritin (Sigma) and transferrin were labeled with Fluorescein isothiocyanate (FITC) (Pierce Biotechnology) in 100 mM carbonate/bicarbonate buffer, pH 9.0. Removal of excess or hydrolyzed FITC was achieved by passage through a 5-ml G-25 desalting column. The FITC-conjugated H-ferritin, spleen ferritin, and transferrin were concentrated and buffer was exchanged with PBS in a CENTRIPREP® concentrator (Amicon, Inc., 10,000 MWCO). Transferrin was included as a positive transport control in the BREC model (Burdo J. R., et al. *Neuroscience* 121: 883-890, 2003).

The rate of flux across a confluent BREC monolayer was determined as described previously in Burdo et al., 2003, with some modifications using the equation: $(Bf/Tj)*(Vb/A) = (Flux)*t$. Briefly, BRECs were grown to confluence in a transwell apparatus before adding 140 µg of either FITC-labeled rH-ferritin, spleen-ferritin, or transferrin to the top chamber (apical). Transport of the tracer is determined by sampling from 100 µl aliquots from the bottom chamber (basal) collected at various times (15, 30, 45, 60, 120, 180, and 240 min) following addition of the tracer to the apical chamber. The aliquots from the basal chamber are then analyzed for fluorescence in a spectro-fluorometer (SPECTRAMAX® GEMINI, to Molecular Devices). The rate of flux is obtained as the slope (cm/s) from the plots of bottom chamber fluorescence per unit amount of top chamber fluorescence (Bf/Tf) versus time (t). Here, Bf, indicative of the amount of tracer transported across the monolayer, is normalized to the volume of the basal chamber (Vb) and also the surface area available for transport (A). The concentration of Tf in the top chamber is does not change significantly over the 4 hours that the experiment is performed, and thus, is considered constant for calculating flux. The amount of fluorescence in the top chamber is obtained from a 100 µl aliquot at the end of the transport assay (4 h).

As a control for paracellular flux, RITC dextran (70 kDa) was added simultaneously to the apical chamber as a control. Dextran is not taken up at an appreciable level by endothelial cells (Raub T. J., et al. *J. Cell Physiol.* 149: 141-151, 1991). Thus, any accumulation of dextran in the basal chamber would be due to paracellular transport. None of the conditions affected the rate of flux of dextran, which was minimal in each condition.

Figure 4A:
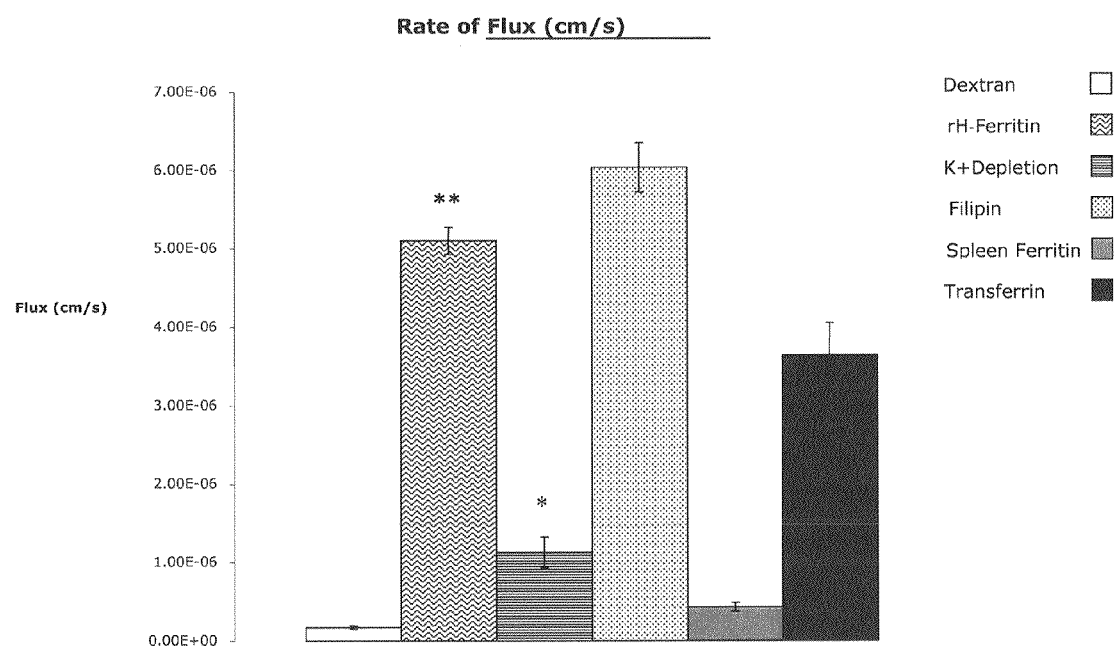
FIG. 4A is a graph showing flux of fluorescein-labeled rH-ferritin across a bovine retinal endothelial cell (BREC) culture monolayer grown in a two-chamber transwell culture dish. The transport rate of FITC-labeled rH-ferritin in the basal chamber over a 4 h period is shown. The rate of transport was determined as described in Example 1. The data are expressed as the means of the rate of flux, obtained as the slope (cm/s) from the plots of bottom chamber fluorescence per unit amount of top chamber fluorescence (Bf/Tf) versus time, and the standard error of the means. rH-ferritin transport is statistically significant compared to the dextran control and spleen ferritin $(p<0.01)^{**}$.
Figure 4B:
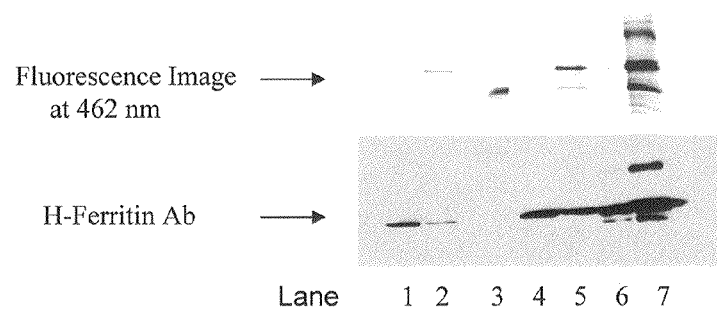
In FIG. 4B, detection of FITC-labeled rH-ferritin in the bottom chamber by fluorescence and specific-binding to H-ferritin antibody is shown. The presence of H-ferritin in the bottom chamber demonstrates that H-ferritin is transcytosed across the BREC cell layer. Lanes: 1) 10 μl concentrated basal chamber medium from control (unlabelled ferritin) cultures; 2) 10 μl concentrated protein from basal chamber medium from FITC-labeled rH-ferritin cultures; 3) molecular weight markers; 4) 30 μl concentrated basal chamber medium from control cultures; 5) 30 μl concentrated protein from basal chamber medium from FITC-labeled rH-ferritin cultures; 6) unlabelled rH-ferritin; 7) FITC-labelled rH-ferritin.

A chemiluminescent system was also used to immunologically detect FITC-labeled rH-ferritin in the basal chamber. Basal medium was collected and concentrated from 1.5 ml to 100 µl using a Centriprep concentrator. The concentrated medium was subjected to SDS-PAGE and the gel was imaged under fluorescence at 462 nm. Subsequently, the proteins were transferred to a membrane and immunoblot analysis was performed with an antibody against rH-ferritin. These experiments demonstrated that the FITC was associated with rH-ferritin, as shown in FIG. 4B.

Determination of Transport Mechanism

To determine if pinocytosis contributed significantly to the transport of ferritin, 50 µg/ml of filipin was added to the apical chambers of the transwell apparatus for 30 minutes before the ferritin and dextran were added. The addition of filipin has been shown to inhibit the action of nonspecific transport via pinocytosis (Stremmel W, et al. *Lipids* 36: 981-989, 2001). To determine if H-ferritin uptake occurs via clathrin-dependent endocytosis, studies were performed in potassium-deficient medium (100 mM NaCl/50 mM HEPES). The cells were incubated in potassium-deficient medium for 10 minutes before the addition of ferritin. Intracellular potassium depletion inhibits receptor-mediated endocytic processes occurring through clathrin-coated pits. These latter experiments could only be performed for one hour before the potassium depletion altered the integrity of the cell-to-cell junctions as indicated by an increase in dextran transport. Each treatment condition (or standard) was performed a minimum of six times. Throughout the experiments the cultures were visually assessed to assure that the experimental treatments and manipulations did not affect cell viability. As in the baseline experiments, RITC dextran was included as an indicator of the integrity of the tight junctions. Differences between the means for FITC rH-ferritin under the different conditions were analyzed using one-way analysis of variance. For those measurements with significantly different means, a Bonferroni post hoc comparison was done to analyze pairwise differences. The level of significance was set at $p<0.05$.

Binding Experiments

The binding experiments on BREC cell homogenates were performed in duplicate on the fourth passage of the BREC cells using $^{125}$I-recombinant human H-ferritin or horse spleen ferritin. The specific activity for both was about 340,000 cpm/pmol. To establish the total specific and non-specific binding, a range of concentrations of $^{125}$I-H-ferritin was added with or without 1000-fold molar excess of unlabeled rH-ferritin to 100 µg total protein of the BREC cell homogenate. The binding buffer consisted of 50 mM Tris-HCl (pH 7.4), 0.1% BSA. Incubations were carried out at 22° C. for 2 h. The binding was terminated by the addition of 3 ml of ice-cold 50 mM Tris-HCl. Using a cell harvester, the bound radioactivity was isolated by rapid filtration and washing over Whatman glass fiber C filters, which were previously coated with 5% non-fat dry milk and 0.1 mg/ml horse spleen ferritin.

Equilibrium competition binding assays were performed, where the increasing concentration of unlabeled H-ferritin was incubated with 25 µg of protein of BREC homogenate at 22° C. with 0.4 nM $^{125}$I-rH-ferritin for 120 minutes in the same binding buffer described before. Termination of binding, isolation of membranes and calculations of specific binding were performed as described above.

Rat Brain Microvasculature

Six adult male rats were used for each microvessel preparation. The rats were anesthetized with a lethal dose of sodium pentobarbital (100 mg/kg body weight) and then decapitated. The brain was removed and placed in a Petri dish on ice. The cerebellum and the meninges were removed and 5 volumes of microvascular buffer (1×MVB, 1× salt, 1×HEPES, 0.5% BSA and 5 mM glucose) with protease inhibitors were added. The brains were gently homogenized with 20 strokes using a glass-teflon homogenizer (0.25 mm clearance) and the homogenate centrifuged at 1000×g for 10 minutes at 4° C. The supernatant was discarded and the pellet resuspended in 5 volumes of 17% dextran (1:1 ratio of 1× salt and 1×HEPES with dextran) followed by vortexing and then centrifugation at 3000×g at 4° C. The microvessels were collected from the wall of the tube and resuspended in 20 ml of 1×MVB buffer. The microvessels were filtered through a 120 µm mesh. Then the microvessel preparation was further purified by adherence to glass beads (Sigma) supported on a 40 µm mesh. The beads were washed with buffer that has protease inhibitors added. The beads were rinsed in 5 ml of MVB and then the microvessels were pelleted by centrifuging at 1000×g at 4° C. for 15 minutes. The microvessels were resuspended in 1 ml of HES+ (10 mM HEPES, 1 mM EDTA, 250 mM sucrose, pH 7.4 and protease inhibitor cocktail) (Sigma) and the total protein concentration determined. The samples were stored at −80° C. until use.

Ferritin Binding on Microvessels

The binding suspension consisted of 50 mM Tris-HCl (pH 7.4), 0.1% BSA, and 20 µg of membrane protein preparation with or without the addition of 1 µM unlabeled rH-ferritin in a final volume of 250 µl. Binding was terminated by the addition of 3 ml of ice-cold 50 mM Tris-HCl. Bound radioactivity was isolated by rapid filtration over Whatman glass-fiber C filters that had been previously coated in a solution of 5% nonfat dried milk (Blotto) with 0.1 mg/ml spleen ferritin. This combination was determined empirically to reduce the nonspecific binding of radiolabeled protein to the filters to 1-3% of the total counts added. The filters were washed 5 times with 3 ml of ice-cold 50 mM Tris containing 200 mM NaCl. The filters were counted in a MICROMEDIC 4/200 plus automatic gamma counter. Specific binding was calculated by subtracting binding in the presence of excess unlabeled rH-ferritin (nonspecific binding) from binding without excess unlabeled rH-ferritin present (total binding).

Saturation Analysis

Each binding experiment was performed in duplicate. Increasing concentrations of $^{125}$I-rH-ferritin were added to binding suspensions consisting of the same binding buffer described previously with 20 µg of membrane protein is preparation with or without the addition of 1 µm unlabeled rH-ferritin in a final volume of 250 µl. After a 120-minute incubation at 22° C., binding was terminated, and total, non-specific, and specific binding were calculated as described above.

Competition Assays

Increasing concentrations of unlabeled competitors (rH-ferritin and spleen ferritin) were incubated for 60 min at 22° C. with 100 µg of membrane protein in the presence of 0.4 nM $^{125}$I-rH-ferritin in the same binding buffer described previously. Binding, termination of binding, isolation of membranes, and calculations of specific binding were performed as described above. The competition experiments were performed in duplicate.

In Vivo Uptake Studies rH- or spleen ferritin (1.2 mg) were incubated in 40 µl of 1 mM nitriolotriacetic acid (pH 6.0), 0.5 µl ferrous ammonium sulfate, 2 µl 0.5M sodium bicarbonate, and 40 µCi of $^{59}$FeCl for 4 hours at 37° C. After incubation, ferritin was dialyzed in a 10,000 MW cartridge in 1×PBS for 24 hours to remove any unbound $^{59}$Fe. The specific activity was 0.04 µCi/g for rH-ferritin and 0.08 µCi/g for spleen ferritin. Radiolabeled protein (3.4 µg/gram wt) was injected (n=3) into the tail vein of female Sprague-Dawley rats (about 350 g body weight). After 48 hrs, the rats were decapitated and the organs removed immediately. Each organ was dissected and rinsed thoroughly in 0.1M PBS. For the brain, the cerebrum was removed from the cerebellum and bisected and the meninges were dissected clear of the brain. One gram of tissue (wet weight) from each organ was used to determine the iron uptake.

H-ferritin-deficient mice were evaluated as an experimental model to determine if potentially compromised iron management in an organ could influence ferritin iron delivery. A similar approach was used to investigate ferritin uptake in control and H-ferritin-deficient mice as described above for the rats except that the mice were injected intraperitoneally. The specific activity for the rH-ferritin was 0.06 μCi/g and for the spleen ferritin was 0.31 μCi/g. Ferritin was injected and allowed to circulate in the bloodstream for 48 hours until the mice were killed and the organs removed.

The amount of radioactivity in each organ was determined on a sodium iodide (NaI) based, single channel analyzer well-counter system (Canberra Industries Inc.) for one minute. The gamma counts/min (cpm) were subtracted from background counts, divided by the efficiency of the counter, and then divided by the disintegration counts/min to calculate μCi. To calculate percent total, organ μCi was divided by total μCi injected then multiplied by 100%.

Results

Figure 1B:
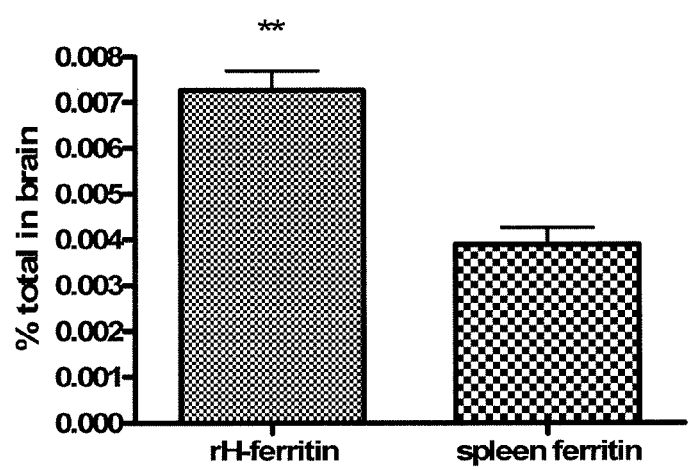
FIG. 1B shows the in vivo uptake of $^{59}$Fe from rH-ferritin in rat brain. Rats were injected via the tail vein with $^{59}$Fe labeled rH- or spleen ferritin as described in the legend for FIG. 1A. The percent total was calculated by determining the μCi in one hemisphere of the brain/total μCi injected×100%. $p<0.005^{**}$. The mean value from 3 animals is presented ±S.E.

In vivo uptake of iron bound to ferritin was examined by injecting rH- or spleen ferritin containing radiolabeled $^{59}$Fe into the tail vein of adult rats. The uptake of iron from rH-ferritin was significantly greater than uptake of iron from spleen ferritin in the brain, heart, kidney, muscle and lung (FIG. 1A). The amount of $^{59}$Fe was two-times higher in the brain when it was presented bound to rH-ferritin compared with spleen ferritin ($p<0.005$) (FIG. 1B). Only the liver had significantly higher uptake of iron from spleen ferritin compared with rH-ferritin ($p<0.05$).

Figure 2A:
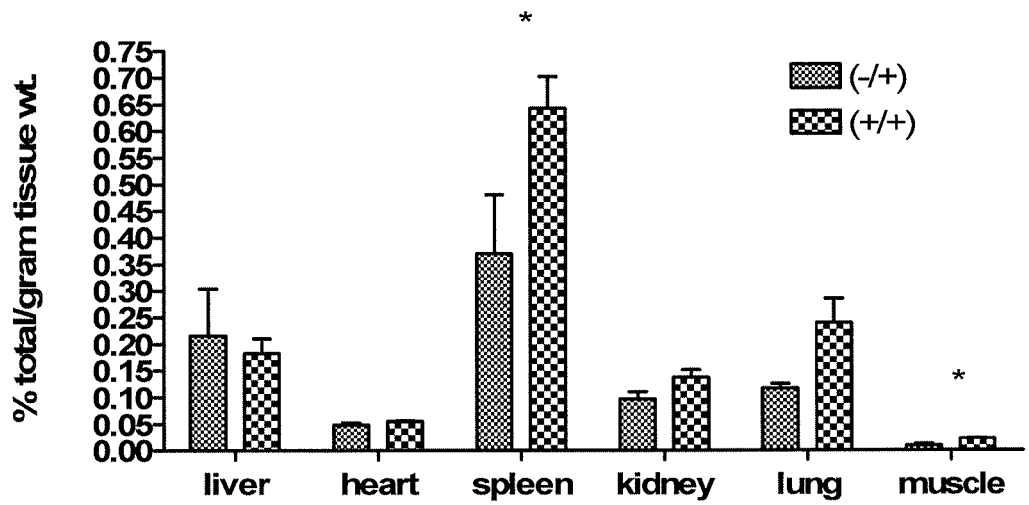
FIG. 2A shows the $^{59}$Fe uptake from rH-ferritin into systemic organs in H-ferritin-deficient mice (−/+) and wild-type (+/+) mice. Animals received equal is amounts of rH-ferritin injected intraperitoneally. The ferritin circulated for 48 hours. The organs shown (including the brain; see FIG. 2B) were removed and the percent of total radioactivity determined for each organ based on 0.1 g. $p<0.05^*$.
Figure 2B:
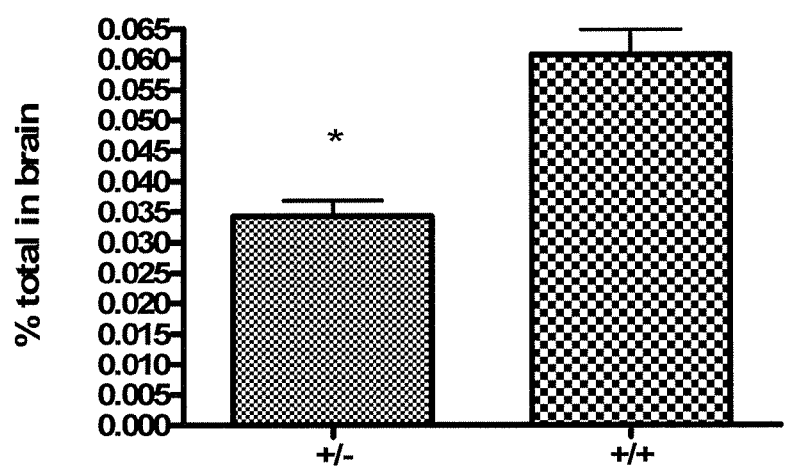
FIG. 2B shows the $^{59}$Fe uptake in brains of H-ferritin-deficient mice (+/−) vs. wild-type (+/+) mice brains delivered via rH-ferritin. These data are from the brains of the mice that were used to generate the data in FIG. 2A. The percent of radioactivity in the brain was determined by comparing the disintegration counts/min of $^{59}$Fe obtained from the brain to the total μCi injected. $p<0.05^*$. The mean value for three animals is shown, ±S.E.
Figure 3A:
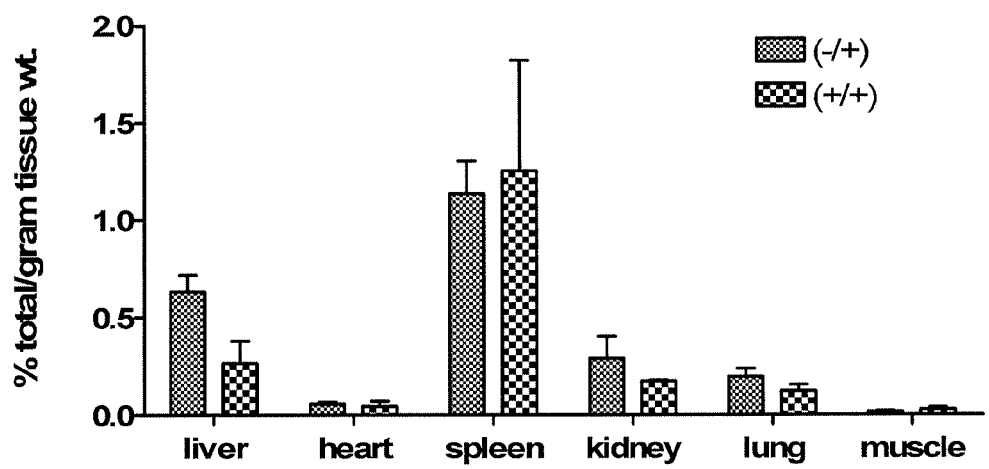
FIG. 3A shows $^{59}$Fe uptake in systemic organs in H-ferritin-deficient (−/+) and wild-type (+/+) mice delivered via spleen (L-enriched) ferritin. Mice were injected intraperitoneally with spleen ferritin containing $^{59}$Fe. After 48 hours the mice were killed and the organs removed. The graph shows percent total radioactivity injected per gram of tissue that is present in each tissue. The mean value from three animals is presented, ±S.E. None of the differences reached statistical significance.
Figure 3B:
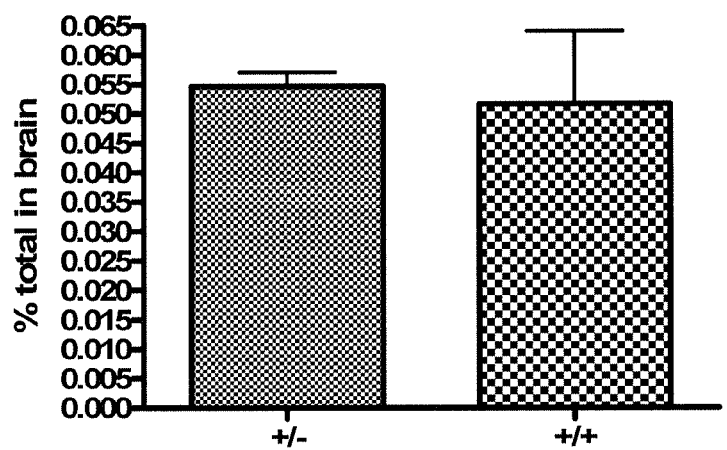
FIG. 3B shows $^{59}$Fe uptake in the brain in H-ferritin-deficient (+/−) vs. wild-type (+/+) mice brains delivered via spleen ferritin. These data are from the mice used in FIG. 3A. The amount of radioactivity reported is the percent of the total injected into the animals. The results present the mean value from three animals, ±S.E. These data failed to show statistical significance.

To determine the influence of potential alterations in iron storage capacity within various organs on rH- and spleen ferritin delivery of iron to various organs, we investigated the uptake of $^{59}$Fe from these proteins in a mouse line that is deficient in H-ferritin (Thompson K. 3., Fried M. G., Zheng Y., Boyer P., Connor J. R. *J Cell Sci.* 115: 2165-2177, 2002). Iron delivery by rH-ferritin was decreased in the spleen, lung and muscle ($p<0.05$) in the H-ferritin compromised mice compared to littermate controls (FIG. 2A). A similar finding was observed in brain (FIG. 2B). Spleen ferritin uptake was unaltered in any organ in the iron storage compromised mice (FIGS. 3A and 3B).

Although serum ferritin could have unrestricted access to systemic organs, to deliver iron to the brain it must cross an endothelial cell barrier (the BBB). To investigate whether ferritin transcytosis occurs, we utilized a cell culture model of the BBB. H-ferritin, but not spleen ferritin, was transported across the BREC cell monolayer in significant amounts (FIG. 4A). The rate of FITC-labeled H-ferritin that was transported across the BREC monolayer was five-times greater than the RITC-labeled dextran ($p<0.001$). The rate of transport of spleen ferritin was similar to the level seen in the dextran control. To determine the mechanism by which H-ferritin is transcytosed we performed the transport assays in a potassium-free medium to block the formation of clathrin-coated vesicles. The absence of clathrin coat formation was associated with an 80% ($p<0.001$) decrease in the rate of H-ferritin transport. In contrast, filipin pretreatment of the BRECs, to block pinocytosis, resulted in no significant decrease in rate. A dextran control was included in each experimental condition and the rate did not change from that shown in the graph for the untreated condition (data not shown). Transferrin transport was included as a positive control and was detected as previously reported (Burdo J. R., Antonetti D. A., Wolpert E. B., Connor J. R. *Neuroscience* 121: 883-890, 2003). The specific activities of fluorescently labeled transferrin and ferritin were different so no conclusions can be made about the relative rates of transport for these two proteins.

To more thoroughly evaluate the mechanism of iron delivery to the brain via ferritin, binding studies were performed to determine if the transport of ferritin in the BREC model was receptor-mediated. In addition, to expand the evaluation of ferritin binding to an in vivo system, microvasculature was isolated from rat brain (RBMVs). Ferritin binding to BREC and RBMVs was performed utilizing a saturation experiment as well as a competition experiment. Kd and Bmax values were obtained using non-linear regression in GRAPHPAD PRISM™ 4.0 (GraphPad Software, Inc.).

Figure 5A:
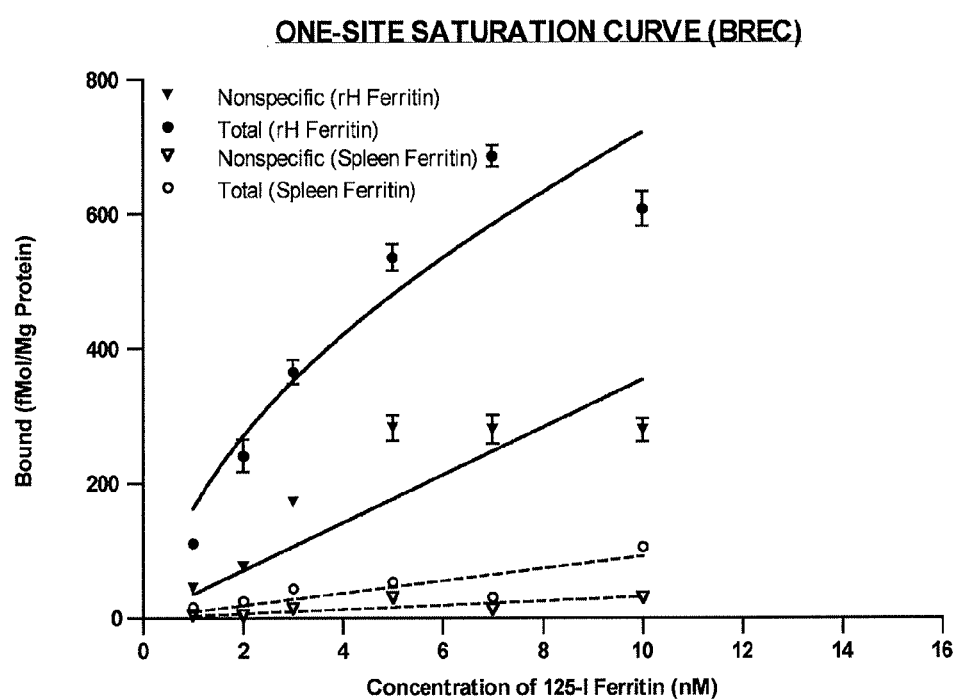
FIG. 5A is a graph showing the saturation curves for $^{125}$I-rH-ferritin and $^{125}$I-spleen-ferritin binding to BREC cell homogenates. This graph illustrates that H-ferritin binding to BREC cells is saturable whereas there is no evidence that spleen ferritin binds to BREC cells. Saturation binding was performed at 4° C. for 2 hours. The Kd was determined to be is 2.7±0.9 nM and the Bmax is 465.7±63.1 fmol/mg protein.
Figure 5B:
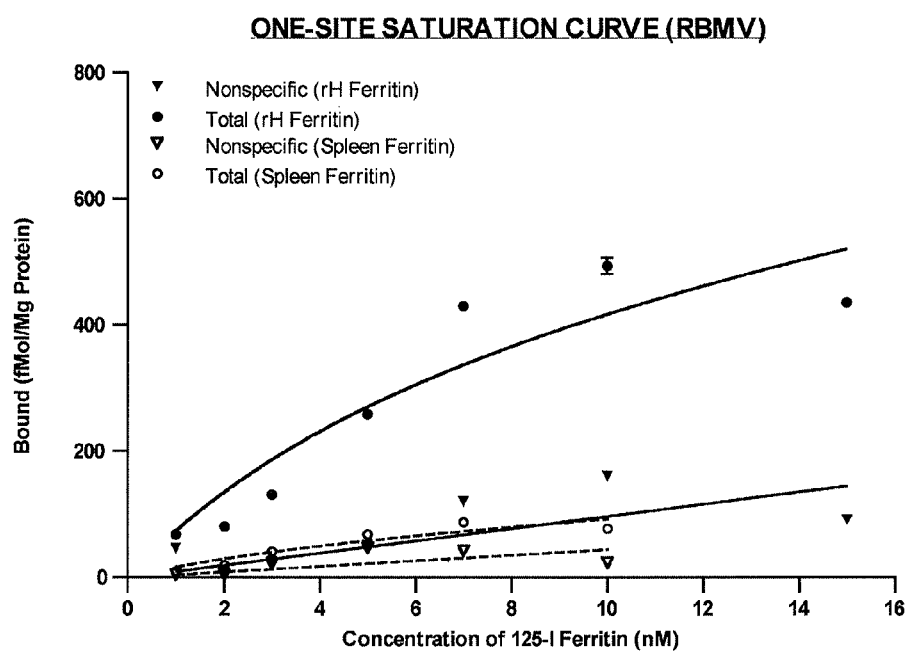
FIG. 5B shows saturation curves for $^{125}$I-rH-ferritin and $^{125}$I-spleen-ferritin on microvessels isolated from rat brains. The curves show saturable binding for H-ferritin, but no binding for spleen ferritin. The Kd is 7.9±1.6 nM and Bmax is 572.6±64.0 fmol/mg protein.

Various concentrations (1, 2, 3, 5, 7, and 10 nM) of $^{125}$I-labeled ferritin (rH-ferritin or spleen ferritin) were incubated with 100 μg of the tissue (BRECs or RBMVs). Total and non-specific binding (in the presence of 1000 nM unlabeled ferritin) were obtained by performing the assay on Whatman filters. To obtain the Kd and Bmax from such a binding assay, non-linear global regression for one-site binding was performed. In this method, both total and non-specific binding were plotted against the concentration of labeled ferritin. The resulting plots were fitted to the equations: Nonspecific=NS*X and Total=Specific+Nonspecific, where, Specific=Bmax*X/(Kd+X). In the global approach, specific binding is not derived to from the total and nonspecific binding data. Instead the values of Kd and Bmax are obtained by sharing the non-specific binding constant (NS) between the two data sets (total and nonspecific). The data from this regression analysis are shown in FIGS. 5A and 5B. Only the rH-ferritin has significant saturable binding to either the BRECs or the RBMVs. The Kd and Bmax for the RBMVs are 7.9±1.6 nM and 572.6±64.0 fmol/mg protein, respectively. For the BRECs, the Kd is 2.7±0.9 nM and the Bmax is 465.7±63.1 fmol/mg protein. The R2 value for the curve fit is >0.8 for both BRECs and RBMVs.

Figure 6A:
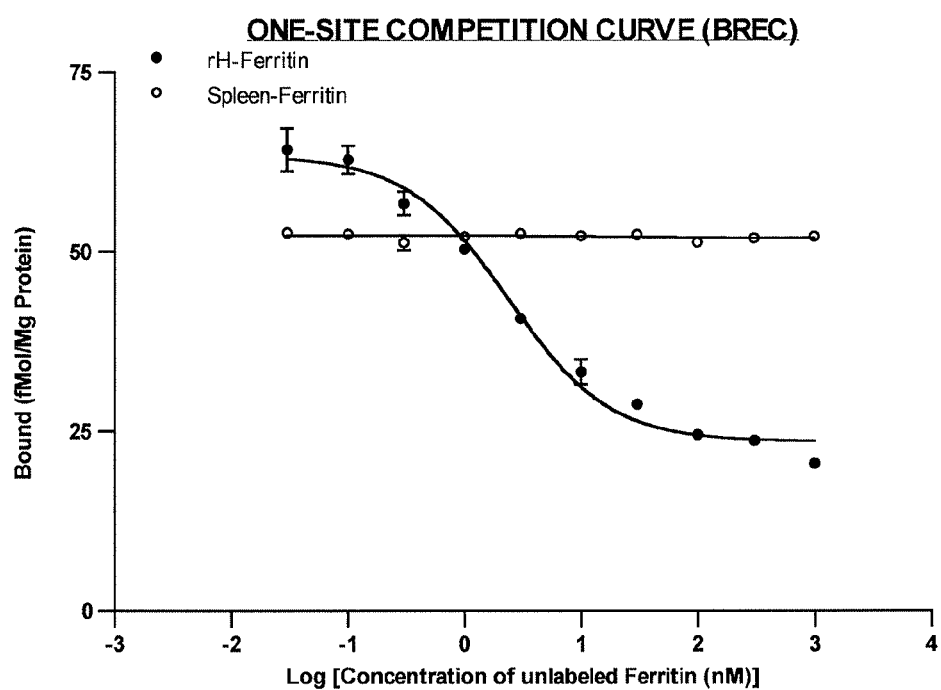
FIG. 6A is a graph showing competition for $^{125}$I-rH-ferritin binding sites on the BREC homogenate by unlabelled rH-ferritin, but not by spleen ferritin. This graph shows that the binding of $^{125}$I-rH-ferritin to the BREC homogenate is competitively inhibited by increasing concentrations of unlabelled rH-ferritin, but not by spleen ferritin.
Figure 6B:
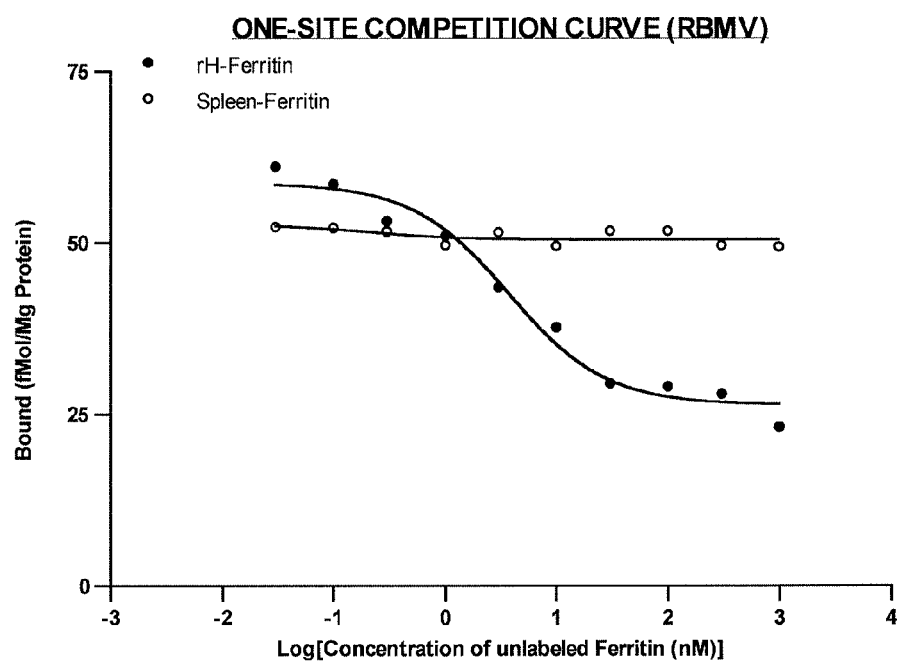
FIG. 6B is a graph showing results from a competition binding assay on rat microvessels. This graph illustrates that binding of $^{125}$I-rH-ferritin can be dissociated in a concentration-dependent manner by unlabeled rH-ferritin but not by unlabeled spleen ferritin.

Various concentrations of unlabeled ferritin (0.03, 0.1, 0.3, 1, 3, 10, 30, 100, 300, and 1000 nM) were incubated with 100 μg of BRECs or RBMV tissue along with 0.4 nM of radiolabeled ferritin. Total binding was obtained by performing the assay on Whatman filters. The total binding (fmol/mg protein) was then plotted against log [concentration (nM)]. These plots were then fit to the one-site competition equation: Total=Bottom+(Top−Bottom)/(1+10 (X−LogEC$_{50}$)). These data are shown in FIGS. 6A and 6B and show that rH-ferritin, but not spleen ferritin, can effectively compete for the binding sites. Determining the Kd and Bmax from the competition curves for the BRECs resulted in Kd of 2.0 nM and Bmax of 235.1 fmol/mg protein. The corresponding values for RBMVs are Kd=3.4 nM and Bmax=304.6 fmol/mg protein. The R2 value for the fit is >0.95 for both BRECs and RBMVs. The two methods used for calculating the data did not differ significantly.

Figure 15:
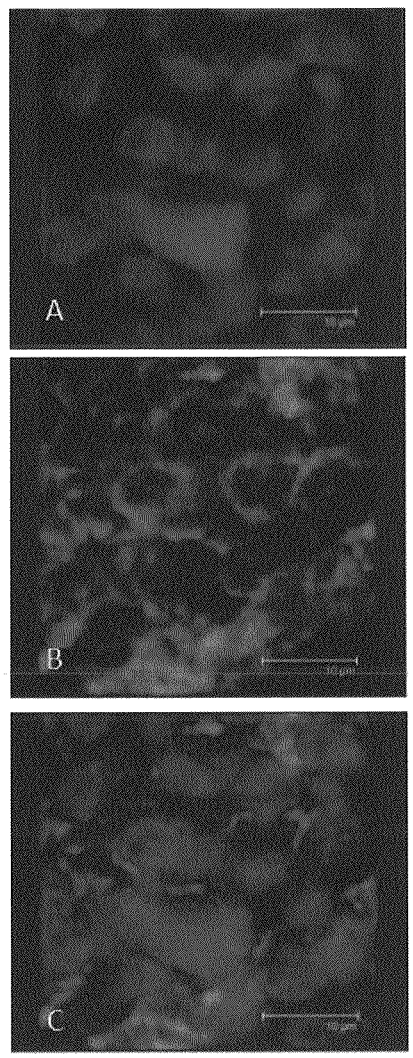
FIG. 15 shows a cross-section of adult rat duodenum localizing immunostained H-ferritin receptors (green) on villi (a and c). Nuclei (blue) are stained with DAPI (b and c). Overlapping images are shown in (c).

A specific receptor for H-ferritin, Tim-2, has been identified which has been found in the brain, liver, kidney, and immune cells (Todorich, et al., *J. Neurochem* 107: 1495-1505, 2008; Chen, et al., *J. Exp. Med.* 202: 955-965, 2005; Chakravarti, et al., *J. Exp. Med.* 202: 437-444, 2005). To determine if this receptor is also present in the gut, an antibody specific for the H-ferritin receptor was used to localize H-ferritin receptor in the rat gut. Adult female rat duodenum was frozen, and 10 μm thick sections prepared for immunocytochemistry. Sections were incubated with primary antibody (Rabbit anti-Tim-2) overnight at 4° C. Sections were washed, and incubated with FITC-labeled IgG secondary antibody at room temperature for one hour. Cell nuclei were stained with DAPI. Sections were examined with a fluorescence microscope. FIG. 15 is a photoimage showing cell nuclei (blue) (a), H-ferritin receptors (green) (b), and double staining in the rat duodenum (c). H-Ferritin receptors are present on the intestinal villi, which to participate in receptor-mediate absorption, demonstrating that H-ferritin can be absorbed intact from the gut.

Discussion

The results of these studies reveal that ferritin can deliver iron to multiple organs including the gut and the brain. Furthermore, the amount of iron delivered is by ferritin is enhanced when the iron is delivered via H-ferritin instead of L-ferritin for most organs except the liver. The amount of H-ferritin iron that is taken up by cells can be altered when iron storage capacity is compromised, as demonstrated in the H-ferritin-deficient mice, whereas iron delivery by L-ferritin is not significantly affected in this model. These results suggest a feedback system for H-ferritin. Thus we have identified a novel transport system for iron delivery to the brain and one that could be highly significant given the amount of iron (up to 4500 Fe atoms) that can be housed in a single molecule of ferritin compared to transferrin (maximum of two Fe atoms). The identification of a non-transferrin-dependent iron delivery system to the brain is consistent with our previous reports showing iron delivery to the brain in the absence of serum transferrin (Malecki, et al., *J Neurosci Res.* 56: 113-122, 1999).

In the brain, in addition to binding to a receptor, ferritin must be transcytosed across the BBB. We demonstrated that ferritin can be transported across a cell culture model of the BBB. The transport of ferritin in this cell culture model is clathrin-dependent and receptor-mediated and strongly favors H-ferritin. The preference for H-ferritin binding is consistent with the transport data. Binding of ferritin was also demonstrated on microvasculature from the rat brain and this binding, similar to the cell culture model, also strongly favored the H-subunit. The binding and transport data are consistent with the iron uptake data that revealed increased delivery to the brain if the iron was associated with H-ferritin relative to spleen (L-rich) ferritin.

The source of ferritin binding the receptors on the BBB and other organs is presumably serum. The presence of ferritin in the serum is well established, but serum ferritin is traditionally considered to be predominantly L-ferritin. The source of this L-rich serum ferritin is primarily from lysed macrophages (McGowan S. E., et al., *J. Lab. Clin. Med.* 111: 611-617, 1988). However, we have surprisingly shown that the binding of ferritin to receptors, transport of ferritin, and delivery of iron to the brain all strongly favor H-rich ferritin.

Example 2

Dietary Delivery of H-Ferritin

Figure 7:
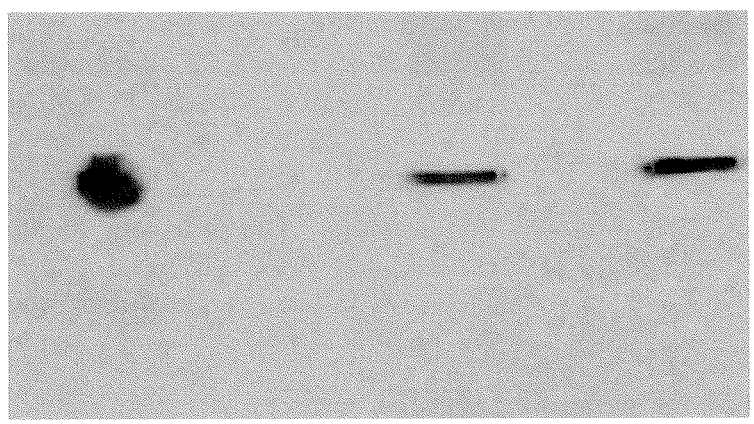
FIG. 7 is a western blot (4-20% gradient) showing expression of rH-ferritin in recombinant yeast. In Lane 1 is a standard (recombinant human H-ferritin). Lanes 2 and 4 are two different colonies of yeast that were transformed with human L-ferritin. Lanes 3 and 5 are two different yeast colonies that were transformed with human H-ferritin. The antibody used in this study is anti-HF HS-59 (1:40,000 for 16 hours), which is a mouse monoclonal to H-ferritin generously supplied by Paolo Arosio (Brescia Italy).
Figure 8:
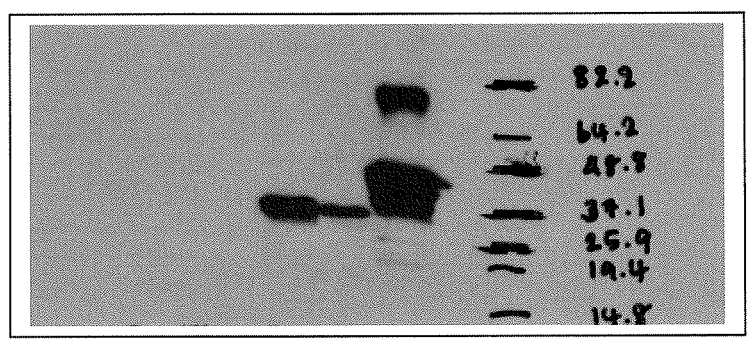
FIG. 8 is a western blot stained for iron. Proteins were first separated by gel electrophoresis and the gel was stained with Perl's reagent, a standard histological stain for iron that is used to demonstrate iron content of ferritin. Lanes 1 and 2 are from yeast colonies that were transformed with L-ferritin. No reaction product for iron is seen in these lanes as L-ferritin is unable to load iron. Lanes 3 and 4 are protein extracts from yeast expressing H-ferritin grown in iron-supplemented medium (Lane 3) and under normal iron medium conditions (Lane 4). An H-ferritin standard was used as a control (Lane 5). Lane 6 contains molecular weight markers to indicate the size of ferritin.

We have devised a mechanism for delivering rH-ferritin as a dietary supplement using recombinant yeast in which the H-ferritin gene is integrated into the yeast genome. Initially, yeast was transformed to express the human H-ferritin gene, which can be translated into the H-ferritin protein. The immunoblot shown in FIG. 7 demonstrates that rH-ferritin protein is produced by the yeast and that the H-ferritin antibody does not cross-react with L-ferritin. A study was performed on the effects of iron concentration in the culture medium on the iron content of rH-ferritin in the transformed yeast. Yeast were grown in YEPD medium containing standard amounts of iron and in iron-supplemented medium (YEPD plus 6 mM $FeSO_4$). The results are shown in FIG. 8. Recombinant yeast for the sample in lane 3 of FIG. 8 were grown in an iron-rich medium, whereas yeast for the sample in lane 4 were grown under standard iron conditions. Ferritin from yeast grown in an iron-rich medium appears to contain 2-3 times as much iron as yeast grown in standard medium.

Methods

Construction of Recombinant Yeast

Figure 16:
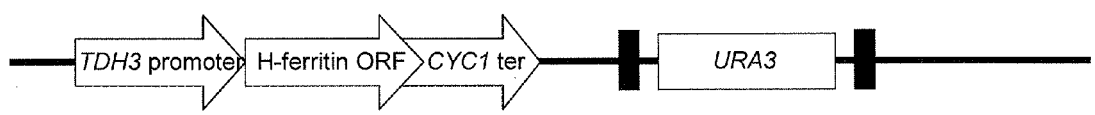
FIG. 16 shows the structure of a gene cassette for expressing H-ferritin under the control of the yeast TDH3 transcriptional promoter. H-ferritin ORF—open-reading frame encoding human H-ferritin; CYC1ter—transcriptional terminator from the yeast CYC1 gene; filled rectangles—loxP sites; URA3—selectable marker.
Figure 17:
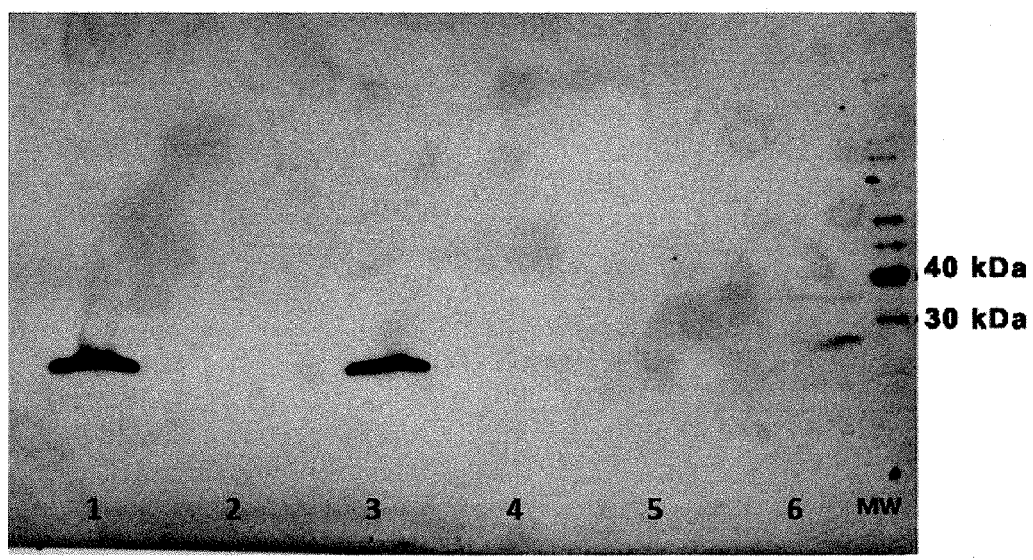
FIG. 17 shows a western blot demonstrating the effect of the chromosomal site of integration on the expression of recombinant H-ferritin in transformed yeast. Lane 1—H-ferritin in RLK3190; Lanes 2 and 4—H-ferritin in yeast strains having other chromosomal integration sites of the H-ferritin gene; Lane 3—H-ferritin in RLK3177, which contains a multicopy, extrachromosomal plasmid; Lane 5—no sample; Lane 6—purified His-tagged rH-ferritin; Lane 7—molecular weight markers.

An H-ferritin expression cassette for *S. cerevisiae*, shown in FIG. 16, expressing human H-ferritin under the control of the yeast constitutive TDH3 transcriptional promoter was generated by PCR from plasmid RLK/pL5659, which was derived from pAG426GPD-ccdB (AddGene, Cambridge, Mass.), by inserting the H-ferritin coding sequence and the URA3 gene. The PCR product was transformed into the yeast strain BY4741 and allowed to integrate into the yeast chromosome using standard methods, for example, as described in Hinnen et al., *PNAS USA* 75: 1929-1933, 1978. Yeast transformants containing the expression cassette were recovered via selectable marker, and lysates of transformed yeast were prepared in 50 mM Tris-HCl (pH 7.4), 150 mM NaCl using glass beads. Twenty-five µg of total protein, determined by the DC Protein Assay (Bio-Rad), were fractionated by SDS-PAGE and to transferred to a nitrocellulose filter. The blot was probed with H-ferritin polyclonal antibody diluted 1:2000 (Covance PA 1192). The secondary antibody was anti-rabbit IgG diluted 1:5000 (GE Amersham) and signal was detected using Western Lightning-ECL (Perkin Elmer). The results, shown in FIG. 17, indicate that the amount of expression of recombinant H-ferritin depends on the site of chromosomal integration. Recombinant strain RLK3190, containing a chromosomally integrated H-ferritin expression cassette, unexpectedly expressed dramatically higher levels of human H-ferritin compared with other chromosomal sites of integration. This level matches or exceeds the amount of H-ferritin produced by strain RLK3177, which contains an extra-chromosomal plasmid bearing multiple copies of the H-ferritin expression cassette. In RLK3190, the expression cassette integrated at the chromosomal location of TDH3 by homologous recombination based on the homology between the TDH3 promoter on the expression cassette and the chromosomal gene. This cassette and others can readily be engineered for insertion at this site using standard techniques in the art.

The expression cassette in the RLK3190 strain constitutively produces human H-ferritin at high levels when it is integrated into the TDH3 locus on the yeast chromosome. When yeast transformants are grown in an iron-rich medium, (for example, 6 mM $FeSo_4$), they attain a cellular iron content of at least 50,000 ppm dry cell weight, a sufficiently high concentration for therapeutic efficacy.

Feeding Studies

Using a standard pre-clinical animal model of iron deficiency, we demonstrated that ferritin-expressing, iron-supplemented yeast are superior to the standard approach of administering ferrous sulfate to treat iron deficiency.

Feeding trials were performed on rats using a well-established rat model. The study was designed to directly compare the efficacy of the ferritin-enriched yeast with the standard for iron replenishment; ferrous sulfate. Twenty-day-old rats were housed 1 per cage and fed an iron-deficient diet (ID; 3 ppm iron). All rats received food and deionized distilled water ad libitum in a temperature—(23±2° C.) and humidity—(40%) controlled room maintained on a 12:12 hr light/dark cycle (lights on 6:00 am to 6:00 pm). The ID diet was prepared following the recipe of the American Institute of Nutrition (AIN)-93G diet with cornstarch as the sole source of carbohydrate. Iron levels of the diet were verified using atomic absorption spectrophotometry after wet digestion with nitric acid A total of 50 µl of blood was collected from each rat every 3-4 days after beginning the ID diet to monitor hematocrit and hemoglobin levels. After 23 days of feeding an iron-deficient diet (postnatal day 43), mean hemoglobin and hematocrit levels were 5.47±0.24 and 21.67±0.3%, respectively. Rats were then randomly divided into 3 groups (n=4/group):

Each diet was prepared with the ID diet (3 ppm iron) as the base diet. Iron supplemented yeast (not expressing ferritin) or iron sulfate was added to the ID diet to 50 ppm to make the control diets. The rats were fed the assigned diets ad libitum, and hemoglobin and hematocrit levels were again measured every 3-4 days until postnatal day 61 (total of 17 days). Food intake was measured for the entire feeding period and was not different between groups. Rats were euthanized at P61 and hematology and brain measurements determined.

Figure 9:
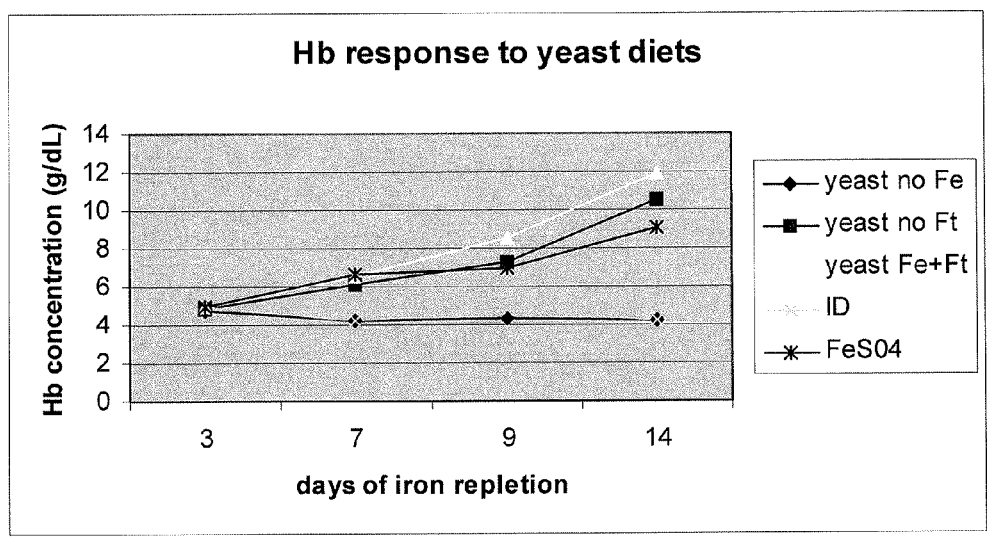
FIG. 9 shows results obtained using a standard rat model of iron deficiency. The animals on an iron-deficient (ID) diet had the lowest levels of hemoglobin (Hb). The animals that received yeast without iron (yeast no Fe) had Hb levels similar to the ID animals. Improvements in the Hb levels were seen in the other three groups with the most rapid increase in improvement occurring in the animals that received the yeast that were iron-supplemented and fortified with H-ferritin (yeast Fe+Ft).

The results are shown in FIG. 9. The animals continuing on the ID diet had the lowest levels of hemoglobin (Hb). The animals that received the yeast without iron had Hb levels similar to the ID animals. Improvements in the Hb levels were seen in the other three groups with the most rapid increase in improvement occurring in the animals that received the yeast that were iron-supplemented and fortified with ferritin. Even the animals receiving iron-supplemented yeast without ferritin showed better improvement in Hb levels than the $FeSO_4$ group.

Figure 10:
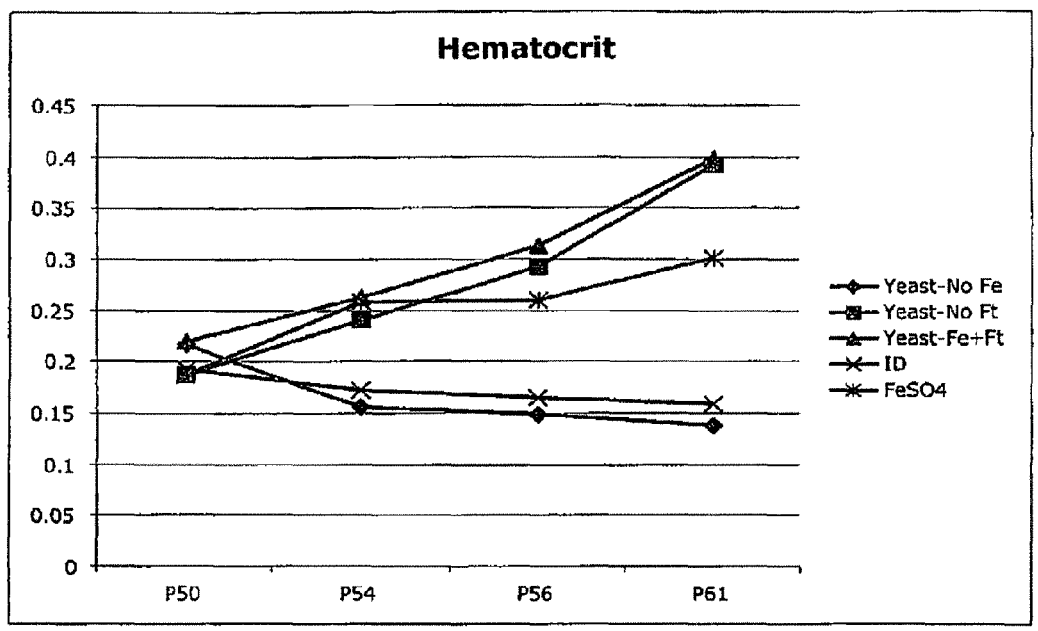
FIG. 10 represents hematocrit levels from the group of animals tested in FIG. 9. These data show that yeast as a vehicle for iron are equally effective at correcting the hematocrit in the presence or absence of H-ferritin and both are significantly better than the standard current treatment option, $FeSO_4$. Animals that continued on the ID diet and animals receiving yeast that had not been iron-supplemented showed no increase in hematocrit over the 11 days examined.

Hematocrit levels were also monitored in the same group of animals. These data are shown in FIG. 10. These data show that yeast as a vehicle for iron are equally effective at correcting the hematocrit in the presence or absence of H-ferritin and both are significantly better than the standard current treatment option, $FeSO_4$. Animals that continued on the ID diet and animals receiving yeast that had not been iron-supplemented showed no increase in hematocrit over the 17 days examined.

Figure 11:
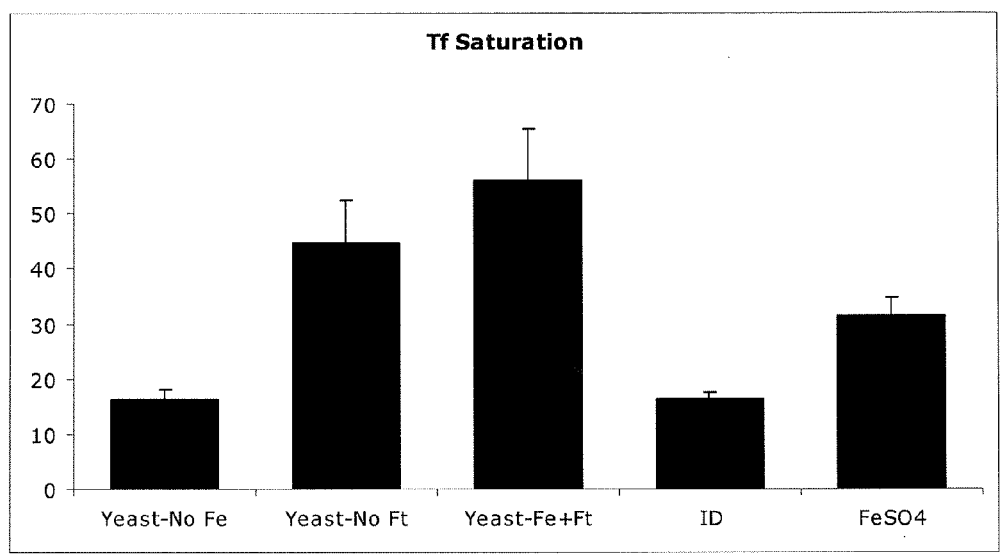
FIG. 11 shows the results of a test measuring iron bioavailability in the group of animals tested in FIGS. 9 and 10. These data show that the ferritin-fortified iron-supplemented yeast (Yeast Fe+Ft) provided the greatest increase in transferrin (Tf) saturation, followed by the iron-supplemented yeast without ferritin (Yeast no Ft). $p<0.05$ for Yeast Fe+Ft vs. all groups except Yeast no Ft.

An important analysis that shows the ability of the body to mobilize the iron, to indirectly a measure of iron bioavailability, is transferrin saturation levels. Transferrin is the main iron mobilization protein and is found in serum in high concentrations. Transferrin saturation fluctuates from a normal high of 30% to less than 10% in conditions of anemia. The analysis of transferrin saturation in the animal model we used to evaluate the efficacy of ferritin-fortified iron-supplemented yeast is shown in FIG. 11. These data show that the ferritin-fortified iron-supplemented yeast resulted in the greatest increase in transferrin (Tf) saturation, followed by the iron-supplemented yeast without ferritin. This study once again demonstrates the superiority of the ferritin-expressing yeast as an iron delivery vehicle compared with $FeSO_4$ in the diet. Animals maintained on the ID diet or fed the control yeast (not iron or ferritin enriched) had the lowest Tf saturations. These studies demonstrate that ferritin-fortified iron-supplemented yeast are up to three times more effective than dietary $FeSO_4$ at improving hemoglobin levels, hematocrit, and iron bioavailability and provide a superior method for treating iron-deficiency disorders. In addition, iron-deficient animals approximated normal hemoglobin (40-50%) and hematocrit (13.5-15.5) levels as early as 14 days after treatment with ferritin-fortified iron-supplemented yeast.

Figure 18:
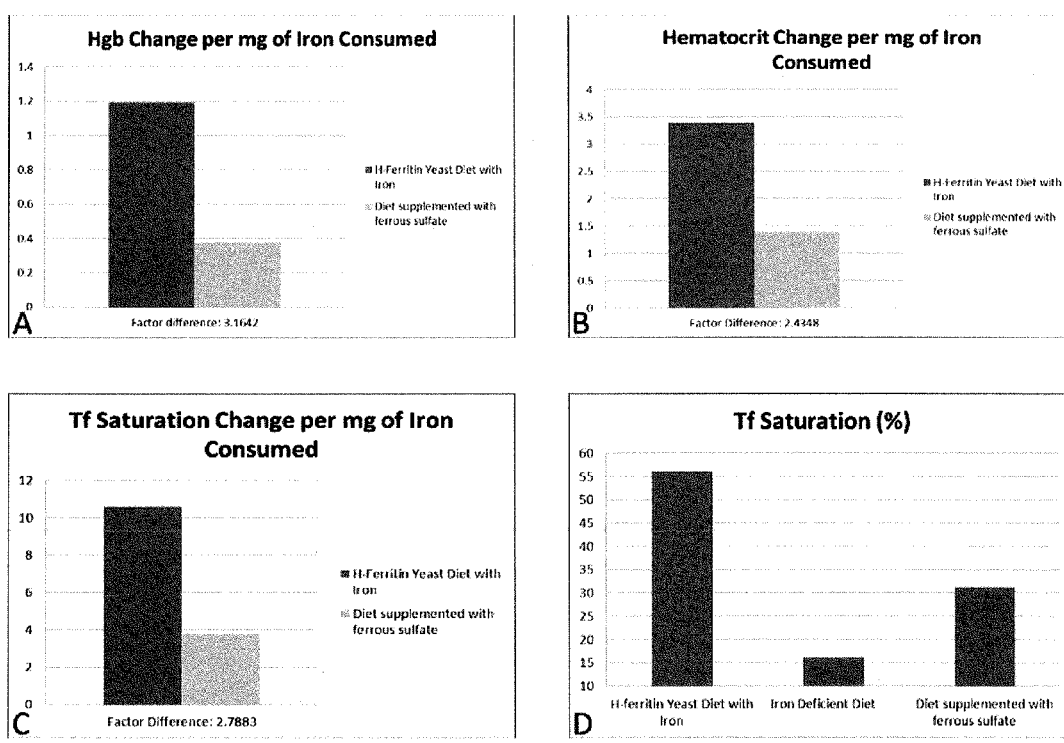
FIG. 18 presents data showing the superior bioavailability of iron delivered by ferritin-fortified iron-supplemented yeast. Day 14 data from the experiments represented by FIGS. 9-11 are graphed to show change per mg of iron consumed. A. Hemoglobin recovery; B. Hematocrit recovery; C. Transferrin saturation; D. Comparison of percent transferrin saturation for different diets, $p<0.05$ for H-ferritin yeast diet with iron vs. other diets.

The surprising superiority of ferritin-fortified iron-supplemented yeast in treating iron deficiency is even more striking when effects on hemoglobin, hematocrit, and transferrin saturation are measured with reference to the amount of iron consumed. As shown in FIG. 18, on the basis of iron consumed, ferritin-fortified iron-supplemented yeast were 2-3 times more effective than $FeSO_4$, the current standard of care, at improving hemoglobin, hematocrit, and transferrin saturation. These results demonstrate that less iron consumption is required to restore normal hemoglobin and hematocrit levels when the bioavailability of iron is increased by using H-ferritin to deliver the iron.

Effects on Brain Iron

Because iron deficiency has a significant impact on brain development, the iron status of specific brain regions was monitored in the animals receiving the different diets. In FIG. 12, the iron status of two developmentally important areas of the brain, the ventral midbrain and the caudate is shown. These areas are destined to become relatively iron enriched as the animal (e.g., human) matures. These brain to regions are involved in regulation of motor activity; hence the impairment of motor skills in iron deficiency, especially when the deficiency occurs during development. The same animals described in the Hb and Hct analyses were killed at 14 days of age and the iron concentration of the ventral midbrain (VBM) and the caudate was measured. The animals receiving the yeast that had been fortified with H-ferritin and supplemented with iron had more in both brain regions than any other group. This exciting finding indicates that the ferritin-fortified dietary supplement may be a mechanism to limit neurological deficits associated with iron deficiency. This observation could have tremendous impact on the war against global iron deficiency not only by increasing general health, but by optimizing neurological function.

To further evaluate regional changes in brain iron status two other areas of the brain, the nucleus accumbens (NA) and prefrontal cortex (PFC), were examined. These results are shown in FIG. 13. In this figure, the regional specificity of the iron delivered from the ferritin-fortified iron-supplemented yeast is apparent. In the NA, similar to the VMB and caudate shown in FIG. 12, the iron content is elevated compared to the other modes of iron delivery. In the PFC, however, the iron delivered from the ferritin-fortified iron-supplemented yeast is similar to that found for the other groups. These data suggest there is a mechanism differentially regulating the iron delivery from ferritin-fortified iron-supplemented yeast and is consistent with our discovery of receptors for H-ferritin on the brain microvasculature.

The increased iron uptake into the brain and, perhaps more importantly, the regional specificity of the uptake are unexpected but highly significant findings associated with the present invention. These data suggest that using ferritin-fortified iron-supplemented yeast should result in improvement of neurological, cognitive and behavioral deficits associated with iron deficiency during postnatal development. The data on hematological parameters are unequivocally strong and indicate that ferritin-fortified iron-supplemented yeast are a superior mode of dietary iron supplementation.

We claim:

1. A method for increasing iron bioavailability in a patient in need of treatment for an iron disorder comprising producing an H-ferritin-iron complex comprising at least one of H-ferritin or a homologue thereof in a yeast comprising a chromosomally-integrated nucleic acid encoding the at least one of an H-ferritin or a homologue thereof, and administering to the patient a therapeutically effective amount of the H-ferritin-iron complex.

2. The method of claim 1, wherein the H-ferritin is mammalian H-ferritin or a homologue thereof.

3. The method of claim 2, wherein the mammalian H-ferritin is human H-ferritin or a homologue thereof.

4. The method of claim 3, wherein the homologue has at least 90% sequence identity with human H-ferritin.

5. The method of claim 1, wherein the iron disorder is iron-deficient anemia.

6. The method of claim 1, wherein the iron disorder is related to an iron deficiency in the brain.

7. The method of claim 1, wherein the iron disorder is a neurological disorder or a neurodegenerative disorder.

8. The method of claim 7, wherein the neurological disorder or the neurodegenerative disorder is selected from the group consisting of Parkinson's disease, Alzheimer's disease, suboptimal cognitive performance associated with anemia in women, depression, insomnia, hypomyelination and slow brain development resulting from developmental iron deficiency leading to poor cognitive performance and motor impairments, attention deficit hyperactivity disorder, multiple sclerosis, restless legs syndrome, attention deficit disorder, and amyotrophic lateral sclerosis.

9. The method of claim 1, wherein the iron disorder comprises at least one of neurological, cognitive, behavioral or motor deficits associated with iron deficiency during postnatal development.

10. The method of claim 1, wherein the H-ferritin-iron complex further comprises a targeting moiety.

11. The method of claim 10, wherein the targeting moiety is selected from the group consisting of an antibody, an aptamer, a receptor, a ligand, and a binding fragment thereof.

12. The method of claim 10, wherein the targeting moiety recognizes a brain-specific marker or a blood-brain-barrier-specific marker.

13. The method of claim 10, wherein the targeting moiety is selected from the group consisting of transferrin, interleukin-13, and lipopolysaccharide.

14. The method of claim 1, wherein the H-ferritin-iron complex is administered as a yeast cell or an extract produced from yeast.

15. The method of claim 1, wherein the chromosomally-integrated nucleic acid encoding at least one of an H-ferritin or a homologue thereof is integrated into the yeast chromosome at the TDH3 site.

16. The recombinant yeast of the method of claim 1 comprising a nucleic acid sequence encoding human H-ferritin integrated into the yeast chromosome and capable of producing human H-ferritin-iron complex for administration to a patient in a therapeutically effective amount for increasing iron bioavailability.

17. The recombinant yeast of claim 16, wherein the nucleic acid sequence encoding human H-ferritin is integrated into the yeast chromosome at the TDH3 site.

18. A composition for orally treating an iron disorder in a patient comprising the recombinant yeast of claim 16.

19. A composition for orally treating an iron disorder in a patient comprising the recombinant yeast of claim 17.

20. A method for delivering a therapeutically effective amount of iron to the brain of a patient in need thereof comprising producing in a yeast an H-ferritin-iron complex comprising at least one of an H-ferritin or a homologue thereof, wherein the yeast comprises a chromosomally-integrated nucleic acid encoding the at least one of an H-ferritin or a homologue thereof; then administering to the patient a therapeutically effective amount of the H-ferritin-iron complex, whereby a therapeutically effective amount of iron is transported across the blood-brain barrier and delivered to the brain.

21. The method of claim 20, wherein the H-ferritin-iron complex is administered as a yeast cell or an extract produced from yeast.

22. The method of claim 20, wherein the chromosomally-integrated nucleic acid encoding at least one of an H-ferritin or a homologue thereof is integrated into the yeast chromosome at the TDH3 site.

23. A method for treating an iron disorder in a patient comprising administering to a patient in need thereof a therapeutically effective amount of an H-ferritin-iron complex comprising human H-ferritin or a homologue thereof produced in a recombinant yeast comprising a nucleic acid sequence encoding human H-ferritin integrated into a yeast chromosome.

24. A method for delivering a therapeutically effective amount of iron to the brain comprising administering to a patient in need thereof an H-ferritin-iron complex comprising human H-ferritin or a homologue thereof produced in a recombinant yeast comprising a nucleic acid sequence encoding human H-ferritin integrated into a yeast chromosome, whereby a therapeutically effective amount of iron is transported across the blood-brain barrier and delivered to the brain.

* * * * *